(12) United States Patent
Van Der Weerden et al.

(10) Patent No.: US 10,231,450 B2
(45) Date of Patent: Mar. 19, 2019

(54) AGENTS AND METHODS FOR TREATMENT OF PATHOGENS

(71) Applicant: Hexima Limited, Victoria (AU)

(72) Inventors: Nicole Van Der Weerden, Coburg (AU); Marilyn Anne Anderson, Keilor (AU)

(73) Assignee: Hexima Limited, La Trobe University, Victoria (AU)

( * ) Notice: Subject to any disclaimer, the term of this patent is extended or adjusted under 35 U.S.C. 154(b) by 21 days.

(21) Appl. No.: 15/306,266

(22) PCT Filed: Apr. 23, 2015

(86) PCT No.: PCT/AU2015/050192
§ 371 (c)(1),
(2) Date: Oct. 24, 2016

(87) PCT Pub. No.: WO2015/161346
PCT Pub. Date: Oct. 29, 2015

(65) Prior Publication Data
US 2017/0049102 A1 Feb. 23, 2017

(30) Foreign Application Priority Data

Apr. 23, 2014 (AU) ................. 2014901470

(51) Int. Cl.
| | | |
|---|---|---|
| *A61K 38/16* | (2006.01) | |
| *A61K 38/17* | (2006.01) | |
| *A01N 37/46* | (2006.01) | |
| *A01N 63/02* | (2006.01) | |
| *A01N 65/38* | (2009.01) | |
| *C07K 14/415* | (2006.01) | |
| *C12N 15/82* | (2006.01) | |
| *A61K 38/01* | (2006.01) | |
| *A61K 8/42* | (2006.01) | |
| *A61Q 5/02* | (2006.01) | |
| *A61Q 17/00* | (2006.01) | |
| *A61Q 19/10* | (2006.01) | |
| *A61K 36/00* | (2006.01) | |

(52) U.S. Cl.
CPC ............ *A01N 37/46* (2013.01); *A01N 63/02* (2013.01); *A01N 65/38* (2013.01); *A61K 8/42* (2013.01); *A61K 38/011* (2013.01); *A61K 38/16* (2013.01); *A61K 38/1729* (2013.01); *A61Q 5/02* (2013.01); *A61Q 17/005* (2013.01); *A61Q 19/10* (2013.01); *C07K 14/415* (2013.01); *C12N 15/8279* (2013.01); *C12N 15/8282* (2013.01); *A61K 36/00* (2013.01)

(58) Field of Classification Search
None
See application file for complete search history.

(56) References Cited

U.S. PATENT DOCUMENTS

2010/0095408 A1* 4/2010 Heath ................. A01N 65/00
800/301

FOREIGN PATENT DOCUMENTS

| WO | WO 2002/063011 A1 | 8/2002 |
|---|---|---|
| WO | WO 2008/128289 A1 | 10/2008 |
| WO | WO 2009/094719 A1 | 8/2009 |
| WO | WO 2010/015024 A1 | 2/2010 |
| WO | WO 2012/027209 A2 | 3/2012 |
| WO | WO 2012/106759 A1 | 8/2012 |
| WO | WO 2014/078900 A1 | 5/2014 |

OTHER PUBLICATIONS

Carvalho, A. de O. and Gomes, V.M. 'Plant Defensins and Defensin-Like Peptides—Biological Activities and Biotechnological Applications', Current Pharmaceutical Design, 2011, vol. 17, pp. 4270-4293.

Van Der Weerden, N.L. and Anderson, M.A. 'Plant Defensins: Common Fold, Multiple Functions'. Fungal Biology Reviews, 2013, vol. 26, pp. 121-131.

* cited by examiner

Primary Examiner — Lianko G Garyu
(74) Attorney, Agent, or Firm — Knobbe, Martens, Olson & Bear, LLP

(57) ABSTRACT

Agents and natural and synthetic formulations and extracts are useful in control of pathogen infection and infestation in humans, animals and plants, as well as pathogen contamination in environmental locales. A method inhibits growth or infection or infestation of a pathogen, including contacting the pathogen with an effective amount of a combination of a plant defensin or a functional natural or synthetic derivative or variant thereof and a non-defensin peptide, such as a cathelicidin peptide, a hairpin peptide, a hairpin peptide from which disulfide bridges have been removed, indolicidin, synthetic peptide CP-29, or a peptide derived from a cystatin. The combination of the defensin and peptide are synergistic compared to the use of each alone at the same individual dose as used in the combination.

13 Claims, 1 Drawing Sheet
Specification includes a Sequence Listing.

SEQUENCE LISTING

```
<160> NUMBER OF SEQ ID NOS: 48

<210> SEQ ID NO 1
<211> LENGTH: 20
<212> TYPE: PRT
<213> ORGANISM: artificial
<220> FEATURE:
<223> OTHER INFORMATION: Amino acid sequence of C-terminal end amino
      acid sequence of NaD1 which ends and includes the most C-terminal
      invariant cysteine residue

<400> SEQUENCE: 1

Lys Phe Thr Asp Gly His Cys Ser Lys Ile Leu Arg Arg Cys Leu Cys
1               5                   10                  15

Thr Lys Pro Cys
            20

<210> SEQ ID NO 2
<211> LENGTH: 6
<212> TYPE: PRT
<213> ORGANISM: artificial
<220> FEATURE:
<223> OTHER INFORMATION: A modified amino acid sequence of a Class II
      Solanaceous defensin Loop1B region
<220> FEATURE:
<221> NAME/KEY: MISC_FEATURE
<222> LOCATION: (1)..(1)
<223> OTHER INFORMATION: X1 = A, R, N, D, C, Q, E, G, H, I, L, K, M, F,
      P, S, T, W, Y or V
<220> FEATURE:
<221> NAME/KEY: MISC_FEATURE
<222> LOCATION: (2)..(2)
<223> OTHER INFORMATION: X2 = A, R, N, D, C, Q, E, G, H, I, L, K, M, F,
      P, S, T, W, Y or V
<220> FEATURE:
<221> NAME/KEY: MISC_FEATURE
<222> LOCATION: (3)..(3)
<223> OTHER INFORMATION: X3 = A, R, N, D, C, Q, E, G, H, I, L, K, M, F,
      P, S, T, W, Y or V
<220> FEATURE:
<221> NAME/KEY: MISC_FEATURE
<222> LOCATION: (4)..(4)
<223> OTHER INFORMATION: X4 = A, R, N, D, C, Q, E, G, H, I, L, K, M, F,
      P, S, T, W, Y or V
<220> FEATURE:
<221> NAME/KEY: MISC_FEATURE
<222> LOCATION: (5)..(5)
<223> OTHER INFORMATION: X5 = A, R, N, D, C, Q, E, G, H, I, L, K, M, F,
      P, S, T, W, Y or V
<220> FEATURE:
<221> NAME/KEY: MISC_FEATURE
<222> LOCATION: (6)..(6)
<223> OTHER INFORMATION: X6 = A, R, N, D, C, Q, E, G, H, I, L, K, M, F,
      P, S, T, W, Y or V
```

```
<400> SEQUENCE: 2

Xaa Xaa Xaa Xaa Xaa Xaa
1 5

<210> SEQ ID NO 3
<211> LENGTH: 6
<212> TYPE: PRT
<213> ORGANISM: artificial
<220> FEATURE:
<223> OTHER INFORMATION: A modified amino acid sequence of a Class II Solanaceous defensin of Loop1B region
<220> FEATURE:
<221> NAME/KEY: MISC_FEATURE
<222> LOCATION: (1)..(1)
<223> OTHER INFORMATION: X1 = N, g, D, H, K, A, E, Q, T, P, L, M, S or R
<220> FEATURE:
<221> NAME/KEY: MISC_FEATURE
<222> LOCATION: (2)..(2)
<223> OTHER INFORMATION: X2 = K, R, G, H, L, N, F, I, S, T or Y
<220> FEATURE:
<221> NAME/KEY: MISC_FEATURE
<222> LOCATION: (3)..(3)
<223> OTHER INFORMATION: X3 = W, Y, H, L, G, F or P
<220> FEATURE:
<221> NAME/KEY: MISC_FEATURE
<222> LOCATION: (4)..(4)
<223> OTHER INFORMATION: X4 = P, K, S, R, H, T, E, V, N, Q, D or G
<220> FEATURE:
<221> NAME/KEY: MISC_FEATURE
<222> LOCATION: (5)..(5)
<223> OTHER INFORMATION: X5 = S, K, Y, F, G or H
<220> FEATURE:
<221> NAME/KEY: MISC_FEATURE
<222> LOCATION: (6)..(6)
<223> OTHER INFORMATION: X6 = P, V, L, T, A, F, N, K, R, M, G, H, I or Y

<400> SEQUENCE: 3

Xaa Xaa Xaa Xaa Xaa Xaa
1 5

<210> SEQ ID NO 4
<211> LENGTH: 6
<212> TYPE: PRT
<213> ORGANISM: artificial
<220> FEATURE:
<223> OTHER INFORMATION: A modified amino acid sequence of a Class II Solanaceous defensin of Loop1B region
<220> FEATURE:
<221> NAME/KEY: MISC_FEATURE
<222> LOCATION: (1)..(1)
<223> OTHER INFORMATION: X1 = N, H, Q, D, K or E
<220> FEATURE:
<221> NAME/KEY: MISC_FEATURE
<222> LOCATION: (2)..(2)
<223> OTHER INFORMATION: X2 = R, H, T, K or G
<220> FEATURE:
<221> NAME/KEY: MISC_FEATURE
<222> LOCATION: (3)..(3)
<223> OTHER INFORMATION: X3 = F, H, Y or W
<220> FEATURE:
<221> NAME/KEY: MISC_FEATURE
<222> LOCATION: (4)..(4)
<223> OTHER INFORMATION: X4 = P, K, S or R
<220> FEATURE:
<221> NAME/KEY: MISC_FEATURE
<222> LOCATION: (5)..(5)
<223> OTHER INFORMATION: X5 = G or F
<220> FEATURE:
<221> NAME/KEY: MISC_FEATURE
<222> LOCATION: (6)..(6)
<223> OTHER INFORMATION: X6 = P, V, I or N

<400> SEQUENCE: 4

```
Xaa Xaa Xaa Xaa Xaa Xaa
1               5

<210> SEQ ID NO 5
<211> LENGTH: 6
<212> TYPE: PRT
<213> ORGANISM: artificial
<220> FEATURE:
<223> OTHER INFORMATION: A modified amino acid sequence of a Class II
      Solanaceous defensin of Loop1B region
<220> FEATURE:

<210> SEQ ID NO 7
<211> LENGTH: 6
<212> TYPE: PRT
<213> ORGANISM: artificial
<220> FEATURE:
<223> OTHER INFORMATION: Amino acid sequence of Loop1B from NaD1

<400> SEQUENCE: 7

Asn Thr Phe Pro Gly Ile
1               5

<210> SEQ ID NO 8
<211> LENGTH: 47
<212> TYPE: PRT
<213> ORGANISM: artificial
<220> FEATURE:
<223> OTHER INFORMATION: HXP4 protein

<400> SEQUENCE: 8

Arg Glu Cys Lys Thr Glu Ser His Arg Phe Lys Gly Pro Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 9
<211> LENGTH: 80
<212> TYPE: PRT
<213> ORGANISM: artificial
<220> FEATURE:
<223> OTHER INFORMATION: HXL001 Zea mays

<400> SEQUENCE: 9

Met Ala Leu Ser Arg Arg Met Ala Ala Pro Val Leu Val Leu Met Leu
1               5                   10                  15

Leu Leu Val Ala Thr Glu Leu Gly Thr Thr Lys Val Ala Glu Ala Arg
            20                  25                  30

His Cys Leu Ser Gln Ser His Arg Phe Lys Gly Leu Cys Met Ser Ser
        35                  40                  45

Asn Asn Cys Ala Asn Val Cys Gln Thr Glu Asn Phe Pro Gly Gly Glu
    50                  55                  60

Cys Lys Ala Glu Gly Ala Thr Arg Lys Cys Phe Cys Lys Lys Ile Cys
65                  70                  75                  80

<210> SEQ ID NO 10
<211> LENGTH: 82
<212> TYPE: PRT
<213> ORGANISM: artificial
<220> FEATURE:
<223> OTHER INFORMATION: HXL002 Triticum aestivum

<400> SEQUENCE: 10

Met Ala Leu Ser Arg Arg Met Ala Ala Ser Ala Leu Leu Leu Leu Val
1               5                   10                  15

Leu Leu Val Ala Thr Glu Met Gly Ala Thr Thr Val Lys Leu Ala Glu
            20                  25                  30

Ala Arg Asp Cys Leu Ser Gln Ser His Lys Phe Lys Gly Ala Cys Leu
        35                  40                  45

Ser Ser Ser Asn Cys Ala Ala Val Cys Arg Thr Glu Asn Phe Pro Asp
    50                  55                  60

```
Gly Glu Cys His Thr His Asn Phe Ala Arg Lys Cys Phe Cys Lys Arg
 65                  70                  75                  80

Ala Cys

<210> SEQ ID NO 11
<211> LENGTH: 77
<212> TYPE: PRT
<213> ORGANISM: artificial
<220> FEATURE:
<223> OTHER INFORMATION: HXL004 Nicotiana benthamiana

<400> SEQUENCE: 11

Met Ala Gly Phe Pro Lys Val Leu Ala Thr Val Phe Leu Thr Leu Met
  1               5                  10                  15

Leu Val Phe Ala Thr Glu Met Gly Pro Met Val Thr Glu Ala Arg Thr
                 20                  25                  30

Cys Glu Ser Gln Ser His Arg Phe Lys Gly Leu Cys Phe Ser Arg Ser
             35                  40                  45

Asn Cys Ala Ser Val Cys His Thr Glu Gly Phe Asn Gly Gly His Cys
         50                  55                  60

Arg Gly Phe Arg Arg Arg Cys Phe Cys Thr Arg His Cys
 65                  70                  75

<210> SEQ ID NO 12
<211> LENGTH: 75
<212> TYPE: PRT
<213> ORGANISM: artificial
<220> FEATURE:
<223> OTHER INFORMATION: HXL007 Cyamopsis tetragonoloba

<400> SEQUENCE: 12

Met Glu Lys Lys Ser Leu Ala Gly Phe Cys Cys Leu Phe Leu Ile Leu
  1               5                  10                  15

Phe Leu Ala Gln Glu Ile Val Val Lys Thr Glu Ala Arg Thr Cys Glu
                 20                  25                  30

Ser Leu Ala Asp Thr Tyr Arg Gly Pro Cys Phe Thr Asp Gly Ser Cys
             35                  40                  45

Asp Asp His Cys Lys Asn Lys Glu His Leu Ile Ser Gly Arg Cys Arg
         50                  55                  60

Asn Asp Phe Arg Cys Trp Cys Thr Arg Asn Cys
 65                  70                  75

<210> SEQ ID NO 13
<211> LENGTH: 77
<212> TYPE: PRT
<213> ORGANISM: artificial
<220> FEATURE:
<223> OTHER INFORMATION: HXL008 picramnia pentandra

<400> SEQUENCE: 13

Met Asp Lys Lys Leu Phe Gly Phe Leu Leu Met Phe Ile Leu Phe
  1               5                  10                  15

Ala Ser Gln Glu Ser Met Val Gln Val Glu Ala Lys Val Cys Thr Lys
                 20                  25                  30

Pro Ser Lys Phe Phe Lys Gly Leu Cys Gly Thr Asp Gly Ala Cys Thr
             35                  40                  45

Thr Ala Cys Arg Lys Glu Gly Leu His Ser Gly Tyr Cys Gln Leu Lys
         50                  55                  60

Gly Phe Leu Asn Ser Val Cys Val Cys Arg Lys His Cys
```

<210> SEQ ID NO 14
<211> LENGTH: 74
<212> TYPE: PRT
<213> ORGANISM: artificial
<220> FEATURE:
<223> OTHER INFORMATION: HXL013 Glycine max

<400> SEQUENCE: 14

Met Glu Arg Lys Thr Phe Gly Phe Leu Phe Leu Leu Leu Val Leu
1               5                   10                  15

Ala Ser Asp Val Thr Val Lys Arg Ala Glu Ala Lys Asp Cys Leu Thr
            20                  25                  30

Arg Arg His Gly Phe Gln Gly Arg Cys Leu Phe Asp Arg Gln Cys Ala
        35                  40                  45

His Val Cys Arg Ser Asp Gly Phe Ile Gly Gly Gln Cys Arg Gly Pro
    50                  55                  60

Leu Arg Lys Cys Phe Cys Ser Arg Pro Cys
65                  70

<210> SEQ ID NO 15
<211> LENGTH: 47
<212> TYPE: PRT
<213> ORGANISM: artificial
<220> FEATURE:
<223> OTHER INFORMATION: HXP34

<400> SEQUENCE: 15

Arg Glu Cys Lys Thr Glu Ser Gln His His Ser Phe Pro Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 16
<211> LENGTH: 47
<212> TYPE: PRT
<213> ORGANISM: artificial
<220> FEATURE:
<223> OTHER INFORMATION: HXP35

<400> SEQUENCE: 16

Arg Glu Cys Lys Thr Glu Ser Asp Thr Tyr Arg Gly Val Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45

<210> SEQ ID NO 17
<211> LENGTH: 46
<212> TYPE: PRT
<213> ORGANISM: artificial
<220> FEATURE:
<223> OTHER INFORMATION: HXP37

<400> SEQUENCE: 17

Arg Glu Cys Lys Thr Glu Ser Glu Gly Trp Gly Lys Cys Ile Thr Lys
1               5                   10                  15

Pro Pro Cys Arg Lys Ala Cys Ile Ser Glu Lys Phe Thr Asp Gly His

```
                20                  25                  30
Cys Ser Lys Ile Leu Arg Arg Cys Leu Cys Thr Lys Pro Cys
        35                  40                  45
```

<210> SEQ ID NO 18
<211> LENGTH: 47
<212> TYPE: PRT
<213> ORGANISM: artificial
<220> FEATURE:
<223> OTHER INFORMATION: HXP58

<400> SEQUENCE: 18

```
Arg Glu Cys Lys Thr Glu Ser Lys Thr Trp Ser Gly Asn Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45
```

<210> SEQ ID NO 19
<211> LENGTH: 49
<212> TYPE: PRT
<213> ORGANISM: artificial
<220> FEATURE:
<223> OTHER INFORMATION: HXP72

<400> SEQUENCE: 19

```
Gly Thr Cys Lys Ala Glu Cys His Arg Phe Lys Gly Pro Cys Ile Asn
1               5                   10                  15

Lys Ala Pro Cys Val Lys Cys Cys Lys Ala Gln Pro Glu Lys Phe Thr
            20                  25                  30

Asp Gly His Cys Ser Lys Ile Leu Arg Arg Cys Leu Cys Thr Lys Pro
        35                  40                  45

Cys
```

<210> SEQ ID NO 20
<211> LENGTH: 47
<212> TYPE: PRT
<213> ORGANISM: artificial
<220> FEATURE:
<223> OTHER INFORMATION: HXP91

<400> SEQUENCE: 20

```
Arg Glu Cys Lys Thr Glu Ser Asp Lys Tyr Arg Gly Pro Cys Ile Thr
1               5                   10                  15

Lys Pro Pro Cys Arg Lys Ala Cys Ile Ser Glu Lys Phe Thr Asp Gly
            20                  25                  30

His Cys Ser Lys Ile Leu Arg Arg Cys Leu Cys Thr Lys Pro Cys
        35                  40                  45
```

<210> SEQ ID NO 21
<211> LENGTH: 47
<212> TYPE: PRT
<213> ORGANISM: artificial
<220> FEATURE:
<223> OTHER INFORMATION: HXP92

<400> SEQUENCE: 21

```
Arg Glu Cys Lys Thr Glu Ser Lys Thr Phe Lys Gly Ile Cys Ile Thr
1               5                   10                  15

Lys Pro Pro Cys Arg Lys Ala Cys Ile Ser Glu Lys Phe Thr Asp Gly
            20                  25                  30
```

```
His Cys Ser Lys Ile Leu Arg Arg Cys Leu Cys Thr Lys Pro Cys
        35                  40                  45
```

<210> SEQ ID NO 22
<211> LENGTH: 47
<212> TYPE: PRT
<213> ORGANISM: artificial
<220> FEATURE:
<223> OTHER INFORMATION: HXP95

<400> SEQUENCE: 22

```
Lys Asp Cys Lys Arg Glu Ser His Arg Phe Lys Gly Pro Cys Ile Thr
1               5                   10                  15

Lys Leu Pro Cys Arg Arg Ala Cys Ile Ser Glu Lys Phe Ala Asp Gly
            20                  25                  30

His Cys Ser Lys Ile Leu Arg Arg Cys Leu Cys Thr Lys Pro Cys
        35                  40                  45
```

<210> SEQ ID NO 23
<211> LENGTH: 48
<212> TYPE: PRT
<213> ORGANISM: artificial
<220> FEATURE:
<223> OTHER INFORMATION: HXP107

<400> SEQUENCE: 23

```
Gln Gln Ile Cys Lys Ala Pro Ser His Arg Phe Lys Gly Pro Cys Phe
1               5                   10                  15

Met Asp Ser Ser Cys Arg Lys Tyr Cys Ile Lys Glu Lys Phe Thr Gly
            20                  25                  30

Gly His Cys Ser Lys Leu Gln Arg Lys Cys Leu Cys Thr Lys Pro Cys
        35                  40                  45
```

<210> SEQ ID NO 24
<211> LENGTH: 80
<212> TYPE: PRT
<213> ORGANISM: artificial
<220> FEATURE:
<223> OTHER INFORMATION: HXL015

<400> SEQUENCE: 24

```
Met Ala Pro Ser Arg Arg Met Val Ala Ser Ala Phe Leu Leu Leu Ala
1               5                   10                  15

Ile Leu Val Ala Thr Glu Met Gly Thr Thr Lys Val Ala Glu Ala Arg
            20                  25                  30

His Cys Leu Ser Gln Ser His Arg Phe Lys Gly Met Cys Val Ser Ser
        35                  40                  45

Asn Asn Cys Ala Asn Val Cys Arg Thr Glu Ser Phe Pro Asp Gly Glu
    50                  55                  60

Cys Lys Ser His Gly Leu Glu Arg Lys Cys Phe Cys Lys Lys Val Cys
65                  70                  75                  80
```

<210> SEQ ID NO 25
<211> LENGTH: 49
<212> TYPE: PRT
<213> ORGANISM: artificial
<220> FEATURE:
<223> OTHER INFORMATION: HXL001 Zea Mays

<400> SEQUENCE: 25

```
Arg His Cys Leu Ser Gln Ser His Arg Phe Lys Gly Leu Cys Met Ser
1               5                   10                  15
```

-continued

```
Ser Asn Asn Cys Ala Asn Val Cys Gln Thr Glu Asn Phe Pro Gly Gly
            20                  25                  30

Glu Cys Lys Ala Glu Gly Ala Thr Arg Lys Cys Phe Cys Lys Lys Ile
        35                  40                  45

Cys

<210> SEQ ID NO 26
<211> LENGTH: 49
<212> TYPE: PRT
<213> ORGANISM: artificial
<220> FEATURE:
<223> OTHER INFORMATION: HXL002 Triticum aestivum

<400> SEQUENCE: 26

Arg Asp Cys Leu Ser Gln Ser His Lys Phe Lys Gly Ala Cys Leu Ser
1               5                   10                  15

Ser Ser Asn Cys Ala Ala Val Cys Arg Thr Glu Asn Phe Pro Asp Gly
            20                  25                  30

Glu Cys His Thr His Asn Phe Ala Arg Lys Cys Phe Cys Lys Arg Ala
        35                  40                  45

Cys

<210> SEQ ID NO 27
<211> LENGTH: 47
<212> TYPE: PRT
<213> ORGANISM: artificial
<220> FEATURE:
<223> OTHER INFORMATION: HXL004 Nicotiana benthamiana

<400> SEQUENCE: 27

Arg Thr Cys Glu Ser Gln Ser His Arg Phe Lys Gly Leu Cys Phe Ser
1               5                   10                  15

Arg Ser Asn Cys Ala Ser Val Cys His Thr Glu Gly Phe Asn Gly Gly
            20                  25                  30

His Cys Arg Gly Phe Arg Arg Arg Cys Phe Cys Thr Arg His Cys
        35                  40                  45

<210> SEQ ID NO 28
<211> LENGTH: 47
<212> TYPE: PRT
<213> ORGANISM: artificial
<220> FEATURE:
<223> OTHER INFORMATION: HXL007 Cyamopsis tetragonoloba

<400> SEQUENCE: 28

Arg Thr Cys Glu Ser Leu Ala Asp Thr Tyr Arg Gly Pro Cys Phe Thr
1               5                   10                  15

Asp Gly Ser Cys Asp Asp His Cys Lys Asn Lys Glu His Leu Ile Ser
            20                  25                  30

Gly Arg Cys Arg Asn Asp Phe Arg Cys Trp Cys Thr Arg Asn Cys
        35                  40                  45

<210> SEQ ID NO 29
<211> LENGTH: 50
<212> TYPE: PRT
<213> ORGANISM: artificial
<220> FEATURE:
<223> OTHER INFORMATION: HXL008 Picramnia pentandra

<400> SEQUENCE: 29

Lys Val Cys Thr Lys Pro Ser Lys Phe Phe Lys Gly Leu Cys Gly Thr
```

```
                1               5                  10                  15
Asp Gly Ala Cys Thr Thr Ala Cys Arg Lys Glu Gly Leu His Ser Gly
                20                  25                  30

Tyr Cys Gln Leu Lys Gly Phe Leu Asn Ser Val Cys Val Cys Arg Lys
        35                  40                  45

His Cys
    50
```

<210> SEQ ID NO 30
<211> LENGTH: 47
<212> TYPE: PRT
<213> ORGANISM: artificial
<220> FEATURE:
<223> OTHER INFORMATION: HXL013 Glycine max

<400> SEQUENCE: 30

```
Lys Asp Cys Leu Thr Arg Arg His Gly Phe Gln Gly Arg Cys Leu Phe
1               5                   10                  15

Asp Arg Gln Cys Ala His Val Cys Arg Ser Asp Gly Phe Ile Gly Gly
                20                  25                  30

Gln Cys Arg Gly Pro Leu Arg Lys Cys Phe Cys Ser Arg Pro Cys
        35                  40                  45
```

<210> SEQ ID NO 31
<211> LENGTH: 49
<212> TYPE: PRT
<213> ORGANISM: artificial
<220> FEATURE:
<223> OTHER INFORMATION: HXL015 Oryza sativa

<400> SEQUENCE: 31

```
Arg His Cys Leu Ser Gln Ser His Arg Phe Lys Gly Met Cys Val Ser
1               5                   10                  15

Ser Asn Asn Cys Ala Asn Val Cys Arg Thr Glu Ser Phe Pro Asp Gly
                20                  25                  30

Glu Cys Lys Ser His Gly Leu Glu Arg Lys Cys Phe Cys Lys Lys Val
        35                  40                  45

Cys
```

<210> SEQ ID NO 32
<211> LENGTH: 48
<212> TYPE: PRT
<213> ORGANISM: artificial
<220> FEATURE:
<223> OTHER INFORMATION: HXL012 Amaranthus retroflexus

<400> SEQUENCE: 32

```
Arg Met Cys Lys Ala Pro Ser Lys Leu Phe Arg Gly Met Cys Gly Ile
1               5                   10                  15

Arg Asp Ser Asn Cys Asp Ser Val Cys Arg Ala Glu Gly Met Ala Ala
                20                  25                  30

Gly Asp Cys His Gly Leu Arg Arg Cys Ile Cys Ser Arg Pro Cys
        35                  40                  45
```

<210> SEQ ID NO 33
<211> LENGTH: 50
<212> TYPE: PRT
<213> ORGANISM: artificial
<220> FEATURE:
<223> OTHER INFORMATION: HXL035 Picramnia pentandra

<400> SEQUENCE: 33

-continued

```
Lys Val Cys Thr Lys Pro Ser Lys Phe Phe Lys Gly Leu Cys Gly Phe
1               5                   10                  15

Asp Arg Asp Cys Thr Val Ala Cys Lys Lys Glu Gly Leu Ala Ser Gly
            20                  25                  30

Phe Cys Gln Asn Lys Gly Phe Phe Asn Val Val Cys Val Cys Arg Lys
        35                  40                  45

Pro Cys
    50
```

<210> SEQ ID NO 34
<211> LENGTH: 50
<212> TYPE: PRT
<213> ORGANISM: artificial
<220> FEATURE:
<223> OTHER INFORMATION: HXL036 Picramnia pentandra

<400> SEQUENCE: 34

```
Lys Val Cys Thr Lys Pro Ser Lys Phe Phe Lys Gly Leu Cys Gly Ala
1               5                   10                  15

Asp Arg Asp Cys Thr Val Ala Cys Lys Lys Glu Gly Leu Ala Thr Gly
            20                  25                  30

Phe Cys Gln Lys Lys Gly Phe Phe Asn Phe Val Cys Val Cys Arg Lys
        35                  40                  45

Pro Cys
    50
```

<210> SEQ ID NO 35
<211> LENGTH: 35
<212> TYPE: PRT
<213> ORGANISM: artificial
<220> FEATURE:
<223> OTHER INFORMATION: Sit HPN 100A Setaria italica

<400> SEQUENCE: 35

```
Lys Gly Asp Leu Gln Trp Cys Arg Met Gly Cys Gln Trp Gln Tyr Gly
1               5                   10                  15

Lys Asp Gln Gly Arg Arg Ser Glu Cys Glu Arg Glu Cys Arg Gln Arg
            20                  25                  30

His Arg Gly
        35
```

<210> SEQ ID NO 36
<211> LENGTH: 37
<212> TYPE: PRT
<213> ORGANISM: artificial
<220> FEATURE:
<223> OTHER INFORMATION: EcAMP1 Echinochloa crus-galli

<400> SEQUENCE: 36

```
Gly Ser Gly Arg Gly Ser Cys Arg Ser Gln Cys Met Arg Arg His Glu
1               5                   10                  15

Asp Glu Pro Trp Arg Val Gln Glu Cys Val Ser Gln Cys Arg Arg Arg
            20                  25                  30

Arg Gly Gly Gly Asp
        35
```

<210> SEQ ID NO 37
<211> LENGTH: 35
<212> TYPE: PRT
<213> ORGANISM: artificial
<220> FEATURE:

<223> OTHER INFORMATION: Osa HPN 86B Oryza sativa

<400> SEQUENCE: 37

```
His Gly Gly Gly Gly Lys Glu Cys Arg Arg Glu Cys Arg Gly Tyr Arg
1               5                   10                  15

Asp Glu Pro Trp Arg Lys Gln Glu Cys Met Arg Gln Cys Glu Trp Arg
            20                  25                  30

Arg His Glu
        35
```

<210> SEQ ID NO 38
<211> LENGTH: 36
<212> TYPE: PRT
<213> ORGANISM: artificial
<220> FEATURE:
<223> OTHER INFORMATION: Sbi HPN 104C Sorghum bicolor

<400> SEQUENCE: 38

```
Gly Glu Gly Arg Arg Lys Cys Arg Glu Arg Cys Glu Arg His His Arg
1               5                   10                  15

Gly Gly Asp Trp Trp Glu Lys Gln Arg Cys Leu Met Asp Cys Lys Ser
            20                  25                  30

Arg Glu Gln Glu
        35
```

<210> SEQ ID NO 39
<211> LENGTH: 29
<212> TYPE: PRT
<213> ORGANISM: artificial
<220> FEATURE:
<223> OTHER INFORMATION: Sbi HPN 1041 Sorghum bicolor

<400> SEQUENCE: 39

```
Asp Arg Cys Gln Lys Gln Cys Gln His Tyr Ser Asp Trp Asp Lys Lys
1               5                   10                  15

Gln Gln Cys Val Arg Asp Cys Arg Gly Arg Gly Ser
            20                  25
```

<210> SEQ ID NO 40
<211> LENGTH: 36
<212> TYPE: PRT
<213> ORGANISM: artificial
<220> FEATURE:
<223> OTHER INFORMATION: Cil HPN 14F Carya illinoinensis

<400> SEQUENCE: 40

```
Asp Pro Gln Gln Gln Tyr His Arg Cys Gln Arg Arg Cys Gln Thr Gln
1               5                   10                  15

Glu Gln Ser Pro Glu Arg Gln Arg Gln Cys Gln Gln Arg Cys Glu Arg
            20                  25                  30

Gln Tyr Lys Glu
        35
```

<210> SEQ ID NO 41
<211> LENGTH: 25
<212> TYPE: PRT
<213> ORGANISM: artificial
<220> FEATURE:
<223> OTHER INFORMATION: Androctonin Androctonus australis

<400> SEQUENCE: 41

```
Arg Ser Val Cys Arg Gln Ile Lys Ile Cys Arg Arg Arg Gly Gly Cys
1               5                   10                  15
```

```
<210> SEQ ID NO 42
<211> LENGTH: 18
<212> TYPE: PRT
<213> ORGANISM: artificial
<220> FEATURE:
<223> OTHER INFORMATION: Polyphemusin (F12I)

<400> SEQUENCE: 42

Arg Arg Trp Cys Phe Arg Val Cys Tyr Arg Gly Ile Cys Tyr Arg Lys
1               5                   10                  15

Cys Arg

<210> SEQ ID NO 43
<211> LENGTH: 26
<212> TYPE: PRT
<213> ORGANISM: artificial
<220> FEATURE:
<223> OTHER INFORMATION: SlCys9N (67-92)

<400> SEQUENCE: 43

Lys Leu His His Leu Thr Leu Glu Val Met Asp Ala Gly Lys Lys Lys
1               5                   10                  15

Leu Tyr Glu Ala Lys Val Trp Val Lys Pro
            20                  25

<210> SEQ ID NO 44
<211> LENGTH: 34
<212> TYPE: PRT
<213> ORGANISM: artificial
<220> FEATURE:
<223> OTHER INFORMATION: SlCys9N (77-110)

<400> SEQUENCE: 44

Asp Ala Gly Lys Lys Leu Tyr Glu Ala Lys Val Trp Val Lys Pro
1               5                   10                  15

Trp Leu Asn Phe Lys Glu Leu Gln Glu Phe Lys His Val Glu Asp Val
            20                  25                  30

Pro Thr

<210> SEQ ID NO 45
<211> LENGTH: 25
<212> TYPE: PRT
<213> ORGANISM: artificial
<220> FEATURE:
<223> OTHER INFORMATION: HvCPI6 (75-99)

<400> SEQUENCE: 45

Lys Arg Val Thr Tyr Leu Ala Gln Ile Tyr Glu His Trp Ser Arg Thr
1               5                   10                  15

Arg Lys Leu Thr Ser Phe Lys Pro Ala
            20                  25

<210> SEQ ID NO 46
<211> LENGTH: 34
<212> TYPE: PRT
<213> ORGANISM: artificial
<220> FEATURE:
<223> OTHER INFORMATION: CC7 (71-104)

<400> SEQUENCE: 46
```

```
Asp Pro Ala Gly Arg Thr Val Pro Tyr Val Ala Val Val Tyr Glu Gln
1               5                   10                  15

Val Trp Thr Arg Thr Arg Gln Leu Ala Ser Phe Asn Pro Val Pro Arg
                20                  25                  30

Ala His

<210> SEQ ID NO 47
<211> LENGTH: 49
<212> TYPE: PRT
<213> ORGANISM: artificial
<220> FEATURE:
<223> OTHER INFORMATION: Petunia hybrida (PhD1A)

<400> SEQUENCE: 47

Ala Thr Cys Lys Ala Glu Cys Pro Thr Trp Asp Gly Ile Cys Ile Asn
1               5                   10                  15

Lys Gly Pro Cys Val Lys Cys Cys Lys Ala Gln Pro Glu Lys Phe Thr
                20                  25                  30

Asp Gly His Cys Ser Lys Ile Leu Arg Arg Cys Leu Cys Thr Lys Pro
            35                  40                  45

Cys

<210> SEQ ID NO 48
<211> LENGTH: 47
<212> TYPE: PRT
<213> ORGANISM: artificial
<220> FEATURE:
<223> OTHER INFORMATION: Nicotiana occidentalis ssp Obliqua

<400> SEQUENCE: 48

Arg Gln Cys Lys Ala Glu Ser Asn Thr Phe Thr Gly Ile Cys Ile Ala
1               5                   10                  15

Lys Pro Pro Cys Arg Gln Ala Cys Ile Arg Glu Lys Phe Thr Asp Gly
                20                  25                  30

His Cys Ser Lys Val Leu Arg Arg Cys Leu Cys Thr Lys Arg Cys
            35                  40                  45
```

AGENTS AND METHODS FOR TREATMENT OF PATHOGENS

INCORPORATION BY REFERENCE TO ANY PRIORITY APPLICATIONS

This application is the U.S. National Phase of International Application No. PCT/AU2015/050192, filed Apr. 23, 2015, designating the U.S. and claiming priority to Australian Patent Application No. 2014901470, filed Apr. 23, 2014. Any and all applications for which a foreign or domestic priority claim is identified here or in the Application Data Sheet as filed with the present application are hereby incorporated by reference under 37 CFR 1.57.

FIELD OF THE INVENTION

The present disclosure relates generally to the control of pathogen infection and infestation in humans, animals and plants, as well as pathogen contamination in environmental locales, and agents and natural and synthetic formulations and extracts useful for same.

BACKGROUND OF THE INVENTION

Bibliographic details of the publications referred to by author in this specification are collected alphabetically at the end of the description.

Reference to any prior art in this specification is not, and should not be taken as, an acknowledgment or any form of suggestion that this prior art forms part of the common general knowledge in any country.

Pathogen infection and infestation can lead to significant health issues in humans, animals and plants.

Crop losses due to plant pathogens such as fungal pathogens, for example, are a major problem in the agricultural industry and each year millions of dollars are spent on the application of fungicides to curb these loses (Oerke and Dehne (2004) *Crop Protection* 23:275-285).

Although chemical pathogenicides have been successful in human and veterinary medicine and in the agricultural sector, there is a range of environmental and regulatory concerns with the continued use of chemical agents to control pathogen infection and infestation. The increasing use of these agents is also providing selective pressure for emergence of resistance in pathogen species. This is of particular concern in relation to the widespread use of antibiotics to treat infection in humans and animals. There is clearly a need to develop alternative mechanisms of controlling infection and infestation in humans, animals and plants by pathogens. This need extends to controlling pathogen contamination in soil and other environmental sites to which humans, animals and plants are exposed.

Humans, animals and plants have evolved various systems to provide some natural protection against pathogen infection and infestation. Whilst innate immune mechanisms have been studied in relation to the species investigated, little is known about the use of components of these systems across different species. In plants, these components include small, disulfide-rich proteins which play a large role in both the constitutive and inducible aspects of plant immunity. They can be categorized into families based on their cysteine arrangements and include the thionins, snakins, thaumatin-like proteins, hevein- and knottin-type proteins, lipid transfer proteins, α-hairpinins and cyclotides as well as defensins.

Plant defensins are small (45-54 amino acids), basic proteins with four to five disulfide bonds (Janssen et al. (2003) *Biochemistry* 42(27):8214-8222). They share a common disulfide bonding pattern and a common structural fold, in which a triple-stranded, antiparallel β-sheet is tethered to an α-helix by three disulfide bonds, forming a cysteine-stabilized αβ motif A fourth disulfide bond also joins the N- and C-termini leading to an extremely stable structure. A variety of functions has been attributed to defensins, including anti-bacterial activity, protein synthesis inhibition and α-amylase and protease inhibition (Colilla et al. (1990) *FEBS Lett* 270(1-2):191-194; Bloch and Richardson (1991) *FEBS Lett* 279(1):101-104). Plant defensins have been expressed in transgenic plants, resulting in increased resistance to target pathogens. For example, potatoes expressing the alfalfa defensin (MsDef1, previously known as alfAFP) showed significant resistance against the fungal pathogen *Verticillium dahliae* compared to non-transformed controls (Gao et al. (2000) *Nat Biotechnol* 18(12):1307-1310). Expression of a Dahlia defensin (DmAMP1) in rice was sufficient to provide protection against two major rice pathogens, *Magnaporthe oryzae* and *Rhizoctonia solani* (Jha et al. (2009) *Transgenic Res* 18(0:59-69).

The structure of defensins consists of seven 'loops', defined as the regions between cysteine residues. Loop 1 encompasses the first β-strand (1A) as well as most of the flexible region that connects this β-strand to the α-helix (1B) between the first two invariant cysteine residues. Loops 2, 3 and the beginning of 4 (4A) make up the α-helix, while the remaining loops (4B-7) make up β-strands 2 and 3 and the flexible region that connects them (van der Weerden et al. (2013) *Cell Mol Life Sci* 70(19): 3545-3570).

Despite their conserved structure, plant defensins share very little sequence identity, with only the eight cysteine residues completely conserved. The cysteine residues are commonly referred to as "invariant cysteine residues", as their presence, location and connectivity are conserved amongst defensins. Based on sequence similarity, plant defensins can be categorized into different groups. Within each group, sequence homology is relatively high whereas inter-group amino acid similarity is low (van der Weerden et al. (2013) *Cell Mol Life Sci* 70(19): 3545-3570).

There are two major classes of plant defensins. Class I defensins consist of an endoplasmic reticulum (ER) signal sequence followed by a mature defensin domain. Class II defensins are produced as larger precursors with C-terminal pro-domains or pro-peptides (CTPPs) of about 33 amino acids. Most of the Class II defensins identified to date have been found in Solanaceous plant species.

Class II Solanaceous defensins are expressed in floral tissues. They include NaD1, which is expressed in high concentrations in the flowers of ornamental tobacco *Nicotiana alata* (Lay et al. (2003) *Plant Physiol* 131(3):1283-1293). The anti-fungal activity of this peptide involves binding to the cell wall, permeabilization of the plasma membrane and entry of the peptide into the cytoplasm of the hyphae (van der Weerden et al. (2008) *J Biol Chem* 283 (21):14445-14452) and induction of reactive oxygen species (Hayes et al. (2014) *Cell Mol Life Sci*. February 2014, on line ISSN 1420-682X).

Expression of NaD1 in cotton enhances the resistance to the fungal pathogens *Fusarium oxysporum* fsp. *vasinfectum* and *Verticillium dahliae*. Under field conditions, plants expressing NaD1 are twice as likely to survive compared to untransformed control plants and the lint yield per hectare is doubled. Despite this, there was still a significant level of disease in the NaD1-expressing plants (Gaspar et al. (2014) *J Exp Bot* February 6 epub).

Class II Solanaceous defensins have variable degrees of activity against fungi. Some Class I defensins exhibit very low anti-fungal activity. Development of resistance to some defensins is also a potential problem. Hithertofore, there has been only limited study on the effects of defensins on human and animal pathogens.

Defensins with highly divergent sequences act via different mechanism of actions. Permeabilization of the plasma membrane is a common feature that is observed for a number of defensins. However, the mechanism of permeabilization and its role in cell death differs between different defensins. Some defensins cause membrane permeabilization at high concentrations, but not at the concentration required for complete growth inhibition. In fact, the concentration of these proteins required to cause significant membrane permeabilization is around 20 times that required for growth inhibition. These proteins do cause slight membrane permeabilization at concentrations required for growth inhibition but only after long time periods (>150 mins). This probably occurs after fungal cell death. The cell-impermeate nucleic acid SYTOX [trade mark] green assay described in U.S. patent application Ser. No. 12/535, 443 has been successfully used as a measure of the rate and extent of permeabilization.

In contrast to some other plant defensins, the plant defensin NaD1 causes significant membrane permeabilization at concentrations corresponding to the IC50. Permeabilization of fungal hyphae by NaD1 begins within 15 minutes and reaches its maximum after 80 minutes (van der Weerden et al. (2010) *J Biol Chem* 285(48):37513-37520). NaD1 also causes some membrane permeabilization at low concentrations that does not cause growth inhibition (van der Weerden et al. (2008) *J Biol Chem* 283(20:14445-14452). Difference in the permeabilization kinetics between defensins is likely due to differences in the mechanism of action of the proteins. Hence, there is a role in using permeabilization assays to select appropriate defensins.

There is a need to develop protocols to more effectively manage pathogen infection and infestation in humans, animals and plants. The ability to facilitate this control of pathogens with reduced application of chemical agents or antibiotics or without need for this application altogether would reduce environmental contamination and consequential concerns over carcinogenicity and reduce selective pressures leading to antibiotic resistance.

SUMMARY OF THE INVENTION

Nucleotide and amino acid sequences are referred to by a sequence identifier number (SEQ ID NO). The SEQ ID NOs correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present disclosure teaches a method for inhibiting growth, infection, infestation or contamination by a pathogen, the method comprising contacting the pathogen with an effective amount of a combination of a plant defensin or a functional natural or synthetic derivative or variant thereof and a non-defensin peptide, the combination of the defensin and the peptide being synergistic compared to the use of each alone at the same individual dose as used in the combination. Reference to a "non-defensin peptide" includes a peptide other than a plant defensin. This term encompasses a "non-plant defensin peptide". In some cases, the peptide has anti-pathogen properties. In other cases, the peptide has no or minimal anti-pathogen activity.

In an embodiment, the plant defensin or its functional natural or synthetic derivative or variant is a permeabilizing defensin such as some Class I defensins and Solanaceous Class II defensins. Examples include NaD1 (*Nicotiana alata* defensin; Q8GTM0), TPP3(tomato defensin; AAA80496), PhD1*Petunia hybrida* defensin 1; Q8H6Q1), PhD1A (SEQ ID NO:47), PhD2 (*Petunia hybrid* defensin 2; Q8H6Q0), FST (flower-specific defensin; p32026), NoD173 (SEQ ID NO:48), HXL001, HXL002, HXL004, HXL007, HXL008, HXL012, HXL013, HXL015, HXL035 and HXL036. In an embodiment, the permeabilizing defensin is a functional natural or synthetic derivative or variant of a defensin. Examples of synthetic variants include where a Loop1B from a Class I defensin replaces the Loop1B from the Solanaceous Class II defensin. These include HXP4, HXP34, HXP35, HXP37, HXP58, HXP72, HXP91, HXP92, HXP95 and HXP107.

The non-defensin peptide encompasses a 4 to 100 amino acid residue peptide or a 0.4 to 12 kD peptide characterized as being an α-helical peptide (e.g. an α-helical cathelicidin peptide), a peptide forming a hairpin stabilized by a disulfide bridge (e.g. α-hairpinins and β-hairpins), a hairpin peptide (e.g. α-hairpinins and β-hairpins) where the stabilizing disulphide bridges have been removed, a peptide with extended conformation, a peptide being enriched with specific amino acid residues and/or a peptide derived from a proteinase inhibitor.

An example of α-helical peptides include cathelicidin peptides derived from human or from a non-human primate or a rodent, porcine, bovine, caprine animal such as LL-37, BMAP28, SMAP29, PMAP23, mCRAMP, RK-31 and KS-30.

Examples of α-helical peptides include LL-37, SMAP29, BMAP28, mCRAMP, RK-31, KS-30 and CP-29.

Examples of β-hairpins include bactenecin, protegrin, tachyplesins (e.g. tachyplesin II), androctonin, polyphemusins (e.g. polyphemusin (F12I), polyphemusin I and polyphemusin II), gomesin, thanatin and brevenins. Examples of α-hairpinins include peptides from plant sources including Sit_HPN_100A, EcAMP1, Osa_HPN_86B, Sbi_HPN_104C, Sbi_HPN_104I, Cil_HPN_14F, BWI-2c(Buckwheat trypsin inhibitor-2c), BWI-2b(Buckwheat trypsin inhibitor-2b), luffin P1 from *Luffa aegyptiaca*,MBP-1(maize basic peptide 1),MiAMP2d (*Macadarnia integrifolia* antimicrobial peptide 2d), C2(Cys-rich domain peptide 2 from Cocurbita maxima) and VhTI(*Veronica hederifolia* trypsin inhibitor).

Examples of synthetic hairpin peptides where the disulfide bonds of a β-hairpin or α-hairpinin are removed by replacing the cysteine residues with alanine residues or serine residues include Bac2A and EcAMP4A.

An example of a peptide enriched for specific amino acids is indolicidin.

Examples of extended conformation peptides include Bac2A, EcAMP4A and indolicidin.

Examples of a peptide derived from a proteinase inhibitor, when the proteinase inhibitor is cystatin, include SlCys9N (67-92), SlCys9N (77-110), HvCPI6 (75-99) and CC7 (71-104).

Peptides not encompassed by the present invention are human and plant defensins which are β-sheet or mixed α-β peptides.

It is surprisingly determined herein that the combination of the plant defensin and the peptide derived from a non-plant source, confers enhanced anti-pathogen properties to humans, animals and plants and can be used to decontaminate environmental locales such as soil.

Nothwithstanding the above, some α-hairpinin and β-hairpin peptides show efficacy on their own against pathogens at a concentration higher than the concentration used in a combination with a plant defensin.

The pathogen may be a fungus or microorganism affecting a human, animal and/or plant. In an embodiment, the pathogen is a fungal pathogen. A fungal pathogen includes yeast and a rust.

Animal including mammalian such as human fungal pathogens include species of *Alternaeria* spp, *Aspergillus* spp, *Candida* spp, *Fusarium* spp, *Trichophyton* spp, *Cryptococcus* spp, *Histoplasma* spp, *Microsporum* spp, *Penicillium* spp, *Pneumocystis* spp *Trichosporon* spp, *Scedosporium* spp, *Paeciliomyces* spp, *Acremonium* spp, *Stachybotrys* spp and Dermatiaceous molds. Specific animal, including mammalian and in particular human pathogens include *Alternaria alternata, Aspergillus fumigatus, Aspergillus niger, Aspergillus flavus, Aspergillus nidulans, Aspergillus paraciticus, Candida albicans, Candida dubliniensis, Candida famata, Candida glabrata, Candida guilliermondii, Candida haemulonii, Candida kefyr, Candida krusei, Candida lusitaniae, Candida norvegensis, Candida parapsilosis, Candida tropicalis, Candida viswanathii, Epidermophyton floccosum, Fusarium oxysporum, Fusarium solani, Fusarium monoliforme, Trychophyton rubrum, Trychophyton mentagrophytes, Trychophyton interdigitales, Trychophyton tonsurans, Cryptococcus neoformans, Cryptococcus gattii, Cryptococcus grubii, Microsporum canis, Microsporum gypseum, Penicillium marneffei, Trichosporon beigelii, Trichosporon asahii, Trichosporon inkin, Trichosporon asteroides, Trichosporon cutaneum, Trichosporon domesticum, Trichosporon mucoides, Trichosporon ovoides, Trichosporon pullulans, Trichosporon loubieri, Trichosporon japonicum, Scedosporium apiospermum, Scedosporium prolificans, Paecilomyces variotii, Paecilomyces lilacinus, Acremonium stricutm, Cladophialophora bantiana, Wangiella dermatitidis, Ramichloridium obovoideum, Chaetomium atrobrunneum, Dactlaria gallopavum, Bipolaris* spp, *Exserohilum rostratum* as well as *Absidia corymbifera, Apophysomyces elegans, Mucor indicus, Rhizomucor pusillus, Rhizopus oryzae, Cunninghamella bertholletiae, Cokeromyces recurvatus, Saksenaea vasiformis, Syncephalastrum racemosum, Basidiobolus ranarum, Conidiobolus coronatus, Conidiobolus incongruus, Blastomyces dermatitidis, Coccidioides immitis, Coccidioides posadasii, Histoplasma capsulatum, Paracoccidioides brasiliensis, Pseudallescheria boydii* and *Sporothrix schenckii.*

Specific pathogens for the major crops include: Corn: *Gibberella zeae* (*Fusarium graminearum*), *Colletotrichum graminicola, Stenocarpella maydi* (*Diplodia maydis*), *Fusarium moniliforme* var. *subglutinans, Fusarium verticilloides, Bipolaris maydis* O, T (*Cochliobolis heterostrophus*), *Exserohilum turcicum* I, II and III, *Cercospora zeae-maydis, Pythium irregulare, Pythium debaryanum, Pythium graminicola, Pythium splendens, Pythium ultimum, Pythium aphanidermatum, Aspergillus* spp, *Aspergillus flavus, Helminthosporium carbonum* I, II and III (*Cochliobolus carbonum*), *Helminthosporium pedicellatum, Physoderma maydis, Phyllosticta maydis, Kabatiella maydis, Cercospora sorghi, Ustilago maydis, Ustilago zeae, Puccinia sorghi, Puccinia polysora, Macrophomina phaseolina, Penicillium oxalicum, Nigrospora oryzae, Cladosporium herbarium, Curvularia lunata, Curvularia inaequalis, Curvularia pallescens, Trichoderma viride, Claviceps sorghi, Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporum maydis, Cephalosporum acremonium*; Soybeans: *Fusarium virguliforme, Fusarium solani, Sclerotinia sclerotiorum, Fusarium oxysporum, Fusarium tucumaniae, Phakopsora pachyrhizi Phytophthora megasperma* f.sp. *glycinea, Phytophthora sojae, Macrophomina phaseolina, Rhizoctonia solani, Sclerotinia sclerotiorum Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotrichum truncatum*), *Corynespora cassiicola, Septoria glycines, Phyllosticta sojicola, Alternaria alternata, Microsphaera diffusa, Fusarium semitectum, Phialophora gregata, Glomerella glycines, Pythium aphanidermatum, Pythium ultimum, Pythium debaryanum*; Canola: *Albugo candida, Alternaria brassicae, Leptosphaeria maculans, Rhizoctonia solani, Sclerotinia sclerotiorum, Mycosphaerella brassicicola, Pythium ultimum, Peronospora parasitica, Fusarium oxysporum, Fusarium avenaceum, Fusarium roseum, Alternaria alternata*; Cotton: *Fusarium oxysporum* f.sp. *vasinfectum, Verticillium dahliae, Thielaviopsis basicola, Alternaria macrospora, Cercospora gossypina, Phoma exigua* (*Ascochyta gossypii*), *Pythium* spp *Rhizoctonia solani, Puccinia scheddardii, Puccinia cacabata, Phymatotrichopsis omnivore*; Canola: *Leptosphaeria maculans, Sclerotinia sclerotiorum, Alternaria brassicae, Alternaria brasicicola, Plasmodiophora brassicae, Rhizoctonia solani, Fusarium* spp, *Pythium* spp, *Phytophthora* spp, *Alternaria* spp, *Peronospora parasitica, Mycosphaerella capsellae* (*Pseudocercosporella capsellae*), *Albugo candida, Phytophtohora megasperma* var. *megasperma, Botrytis cinerea, Erysiphe cruciferarum*; Wheat: *Cochliobolus sativus, Drechslera wirreganensis, Mycosphaerella graminicola, Phaeosphaeria avenaria* f.sp. *triticea, Phaeosphaeria nodorum, Blumeria graminis* f.sp. *tritici, Urocystis agropyri, Alternaria alternata, Cladosporium herbarum, Fusarium graminearum, Fusarium avenaceum, Fusarium culmorum, Fusarium pseudograminearum, Ustilago tritici, Ascochyta tritici, Cephalosporium gramineum, Colletotrichum graminicola, Erysiphe graminis* f.sp. *tritici, Puccinia graminis* f.sp. *tritici, Puccinia recondita* f.sp. *tritici, Puccinia striiformis, Puccinia triticina, Sclerophthora macrospora, Urocystis agropyri, Pyrenophora tritici-repentis, Pyrenophora semeniperda, Phaeosphaeria nodorum, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium* spp, *Pythium aphanidermatum, Pythium arrhenomannes, Pythium gramicola, Pythium ultimum, Bipolaris sorokiniana, Claviceps purpurea, Tapesia yallundae, Tilletia tritici, Tilletia laevis, Tilletia caries, Tilletia indica, Ustilago tritici, Wojnowicia graminis, Cochliobolus sativus*; Sorghum: *Exserohilum turcicum, Colletotrichum sublineolum, Cercospora sorghi, Gloeocercospora sorghi, Ascochyta sorghina, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Ramulispora sorghi, Ramulispora sorghicola, Phyllachara saccari, Sporisorium reilianum* (*Sphacelotheca reiliana*), *Sphacelotheca cruenta, Sporisorium sorghi, Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium*

*oxysporum, Pythium arrhenomanes, Pythium graminicola*; Sunflower: *Plasmopara halstedii, Sclerotinia sclerotiorum, Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthe, Verticillium dahliae, Cephalosporum acremonium, Phytophthora cryptogea, Albugo tragopogonis*; Alfalfa: *Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Verticillium albo-atrum, Aphanomyces euteiches, Stemphylium herbarum, Stemphylium alfalfae, Colletotrichum trifolii, Leptosphaerulina briosiana, Uromyces striatus, Sclerotinia trifoliorum, Stagonospora meliloti, Stemphylium botryosum* and *Leptotrichila medicaginis*.

The defensin and the non-defensin peptide may be topically applied to the human, animal or plant or systemically administered to the human or animal or one or both could be expressed in a plant genetically engineered to produce the defensin and/or the peptide. In an embodiment, one is expressed in a plant and the other is topically applied. In another embodiment, one of or both are expressed in genetically modified microorganisms which are then applied to plant seeds. This is particularly useful for protecting plant roots and seeds from fungal or microorganism infestation. In yet another embodiment, a material such as soil or a solid surface such as a door handle or table surface or other environmental locale is decontaminated or otherwise sanitized against current or potential future contamination with a pathogen by the use of the defensin and peptide in combination.

Further taught herein is a formulation or extract comprising both the defensin and the non-defensin peptide or a combination of formulations or extracts each comprising one of the defensin or the peptide. The formulations are then combined prior to or during use. In addition, the extract may contain one of the defensin or peptide and the other component added to the extract. Hence, plant and microbial extracts such as in the form of herbal formulations and natural body washes and shampoos form part of the present invention.

Enabled herein is a use of a plant defensin and a non-defensin peptide in the manufacture of a medicament for the treatment or prophylaxis of pathogen infestation of a human, animal or plant or pathogen contamination in or on material. Also taught here is a plant defensin and a non-defensin peptide for use in the treatment or prophylaxis of pathogen infestation of a human, animal or plant or pathogen contamination in or on material.

Further enabled herein is a use of an α-hairpinin or β-hairpin in the manufacture of a medicament for the treatment or prophylaxis of pathogen infestation of a human, animal or plant or pathogen contamination in or on material. Also taught here is a α-hairpinin or β-hairpin for use in the treatment or prophylaxis of pathogen infestation of a human, animal or plant or pathogen contamination in or on material. In relation to this aspect the concentration of α-hairpinin or β-hairpin is greater than the concentration used when in combination with a plant defensin.

Plants which may be treated include crop plants, ornamental plants, flowering plants, trees, shrubs and grasses. In this regard, the present disclosure extends to genetically modified (transgenic) plants and their progeny. These plants are engineered to express a defensin and a non-defensin peptide, neither of which is naturally expressed in the plant or, alternatively not expressed at the requisite level in a non-engineered plant. In another embodiment, the transgenic plant expresses the non-defensin peptide. In use, the defensin is exogenously supplied to that plant. In the case where the defensin is exogenously supplied, then the plant may also naturally produce the defensin. Animals which may be treated include farm animals, companion animals, laboratory test animals and wild animals. Humans which can be treated include a human of any age. Material which can be treated includes soil, an environmental sample, a door handle and a table surface.

Further contemplated herein is an isolated microorganism engineered to express one or other or both of the defensin and/or non-defensin peptide. Compositions comprising a mixture of microorganisms each producing one or other or both of the defensin and the peptide are further taught herein. Such compositions are useful to treat humans, animals and plants as well as seed sand roots of plants in situ. Alternatively, the defensin and/or the peptide is/are provided as a cell extract including a plant extract or microbial extract.

A kit comprising compartments each containing at least one of plant defensin or a functional natural or synthetic derivative or variant thereof or a non-defensin peptide is also taught herein. Assays to detect suitable defensins, peptides and optimal concentrations are also contemplated herein. The kit may also comprise genetically engineered microorganisms expressing one or other or both of the defensin or non-defensin peptide or a cell extract.

TABLE 1

Summary of sequence identifiers

| SEQUENCE ID NO: | DESCRIPTION |
|---|---|
| 1 | Amino acid sequence of C-terminal end amino acid sequence of NaD1 which ends and includes the most C-terminal invariant cysteine residue |
| 2 | A modified amino acid sequence of Class II Solanaceous defensin Loop 1B region |
| 3 | A modified amino acid sequence of Class II Solanaceous defensin Loop 1B region |
| 4 | A modified amino acid sequence of Class II Solanaceous defensin Loop 1B region |
| 5 | A modified amino acid sequence of Class II Solanaceous defensin Loop 1B region |
| 6 | A modified amino acid sequence of Class II Solanaceous defensin Loop 1B region |
| 7 | Amino acid sequence of Loop1B from NaD1 |
| 8 | Amino acid sequence of full length HXP4 protein |
| 9 | Amino acid sequence of full length HXL001 protein |
| 10 | Amino acid sequence of full length HXL002 protein |
| 11 | Amino acid sequence of full length HXL004 protein |
| 12 | Amino acid sequence of full length HXL007 protein |
| 13 | Amino acid sequence of full length HXL008 protein |
| 14 | Amino acid sequence of full length HXL013 protein |
| 15 | Amino acid sequence of HXP34 protein |
| 16 | Amino acid sequence of HXP35 protein |
| 17 | Amino acid sequence of HXP37 protein |
| 18 | Amino acid sequence of HXP58 protein |
| 19 | Amino acid sequence of HXP72 protein |
| 20 | Amino acid sequence of HXP91 protein |
| 21 | Amino acid sequence of HXP92 protein |
| 22 | Amino acid sequence of HXP95 protein |
| 23 | Amino acid sequence of HXP107 protein |
| 24 | Amino acid sequence of full length HXL015 protein |
| 25 | Amino acid sequence of mature HXL001 protein |
| 26 | Amino acid sequence of mature HXL002 protein |
| 27 | Amino acid sequence of mature HXL004 protein |
| 28 | Amino acid sequence of mature HXL007 protein |

TABLE 1-continued

Summary of sequence identifiers

| SEQUENCE ID NO: | DESCRIPTION |
|---|---|
| 29 | Amino acid sequence of mature HXL008 protein |
| 30 | Amino acid sequence of mature HXL013 protein |
| 31 | Amino acid sequence of mature HXL015 protein |
| 32 | Amino acid sequence of mature HXL012 protein |
| 33 | Amino acid sequence of mature HXL035 protein |
| 34 | Amino acid sequence of mature HXL036 protein |
| 35 | Sit HPN 100A |
| 36 | EcAMP1 |
| 37 | Osa HPN 86B |
| 38 | Sbi HPN 104C |
| 39 | Sbi HPN 104I |
| 40 | Cil HPN 14F |
| 41 | Androctonin |
| 42 | Polyphemusin (F12I) |
| 43 | SlCys9N (67-92) |
| 44 | SlCys9N (77-110) |
| 45 | HvCPI6 (75-99) |
| 46 | CC7 (71-104) |
| 47 | Amino acid sequence of mature PhD1A protein |
| 48 | Amino acid sequence of mature NoD173 protein |

BRIEF DESCRIPTION OF THE DRAWINGS

Some figures contain color representations or entities. Color photographs are available from the Patentee upon request or from an appropriate Patent Office. A fee may be imposed if obtained from a Patent Office.

DETAILED DESCRIPTION OF THE INVENTION

Figure 1:
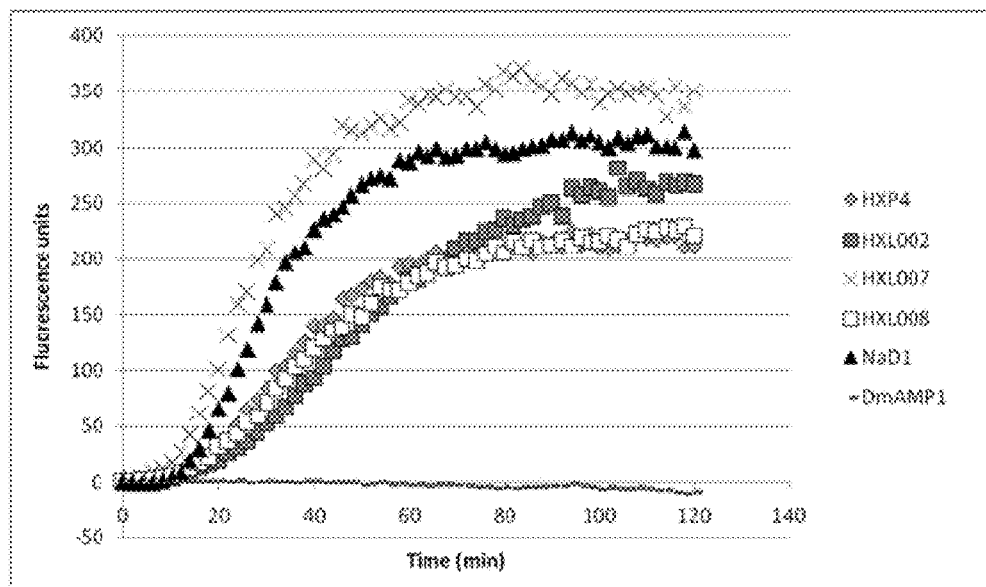
FIG. 1 is a graphical representation of the relative uptake of the green nucleic acid fluorescent dye, SYTOX green [trade mark], into *Fusarium oxysporum* f.sp. *vasinfectum* (Fov) treated with NaD1, HXP4, HXL002, HXL007, HXL008 and DMAMP1. Reference can also be made to Table 2.

Throughout this specification, unless the context requires otherwise, the word "comprise" or variations such as "comprises" or "comprising", will be understood to imply the inclusion of a stated element or integer or method step or group of elements or integers or method steps but not the exclusion of any element or integer or method step or group of elements or integers or method steps.

As used in the subject specification, the singular forms "a", "an" and "the" include plural aspects unless the context clearly dictates otherwise. Thus, for example, reference to "a defensin" includes a single defensin, as well as two or more defensins; reference to "an agent" includes single agent, as well as two or more agents; reference to "the disclosure" includes a single and multiple aspects taught by the disclosure; and so forth. Aspects taught and enabled herein are encompassed by the term "invention". All such aspects are enabled within the width of the present invention.

A protocol is developed to facilitate management of pathogen infection and infestation in human and animal subjects and in plants and to control pathogen contamination in environmental locales. The protocol comprises the use of a plant defensin or a functional natural or synthetic derivative or variant thereof and a non-plant defensin peptide. It is proposed herein that the plant defensin and the peptide act in synergy to provide an efficacious treatment and prophylaxis protocol against pathogens which infect a human or animal subject or a plant or which contaminate an environmental site. The peptide is other than a plant defensin and is referred to as a non-defensin peptide or non-plant defensin peptide. Furthermore, in an embodiment, the non-defensin peptide has anti-pathogen properties. In another embodiment, the peptide on its own has no or minimal anti-pathogen properties.

Hence, enabled herein is a method for inhibiting growth, infection, infestation or contamination by a pathogen, the method comprising contacting the pathogen with an effective amount of a combination of a plant defensin or a functional natural or synthetic derivative or variant thereof and a non-plant defensin peptide, the combination of the defensin and the peptide being synergistic compared to the use of each alone at the same individual dose as used in the combination. For convenience, a human, animal or plant subject may also be referred to as a "host". The defensin and peptide are each also referred to as the "agent" or collectively as the "agents".

In accordance with the subject invention, the inhibitory effect of a given defensin or peptide alone is greater when both are used together compared to either used alone. Greco et al. (1995) *Pharmacol Rev.* 47:331-385 define a category of synergy on the basis that the use of two agents in combination has greater activity relative to the additive effects when each is assayed alone. Hence, the definition adopted herein includes all such situations provided that the combined effect of the two agents acting together is greater than the sum of the individual agents acting alone. Furthermore, a combination of agents is deemed synergistic, as the term is intended herein, if there exists a set of conditions, including but not limited to concentrations, where the combined effect of the agents acting together is greater than the sum of the individual components acting alone. Richer (1987) *Pestic Sci* 19:309-315 describes a mathematical approach to establish proof of synergy. This approach uses Limpel's formula for comparing an observed level of inhibition (Io) in the combined presence of two inhibitor agents, X and Y, with an expected additive effect (Ee) resulting from each X or Y acting separately at the same respective concentrations as used to measure their combined effect. Additive percent inhibition, Ee, is calculated as $X+Y-XY/100$ where X and Y are expressed as percent inhibition. Synergism exits where Io>Ee. It should be noted that the non-defensin peptide may or may not exhibit anti-pathogen properties on its own.

Synergy may be expressed as a synergy scale. In an embodiment, a value of up to 14 represents no significant synergy such as 0, 1, 2, 3, 4, 5, 6, 7, 8, 9, 10, 11, 12, 13 or 14; a value of from 15 up to 29 represents low synergy such as 15, 16, 17, 18, 19, 20, 21, 22, 23, 24, 25, 26, 27, 28 or 29; a value of from 30 to 60 represents medium synergy such as 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60; a value greater than 60 represents a high degree of synergy. By "greater than 60" includes from 61 to 100 including 61, 70, 80, 90 and 100 and any value in between.

As indicated above, a "synergistic effect" occurs where two or more agents within the disclosed protocol produce a combined effect that is greater than the sum of the individual effects of each agent acting alone. This includes the case where the non-defensin peptide exhibits no anti-pathogen properties on its own. The effect may be one or more of efficacy, stability, rate, and/or level of toxicity. As described herein, inhibition of pathogen growth is considered synergistic when, measured in the combined presence of at least one plant defensin and at least one peptide inhibition is greater than the summed inhibition measured in the presence of a particular concentration range of each agent, defensin and the peptide, individually, under otherwise identical conditions. It will be understood that it is not necessary that a greater than additive effect be observed with every combination of concentrations of the two agents in order to be deemed synergistic. The synergistic effect of the two agents can be observed under certain concentration combinations, but not in others. For example, if entry into the pathogen limits toxicity, the presence of defensin can result in synergy, especially if the concentration of the peptide is sub-maximal with respect to inhibition. In one embodiment, the concentration of one or both of the defensin and peptide is sub-maximal. By the same token, synergy can be masked if one or both components is present at such a high level (maximum level) as to result in maximum observable inhibition. The general system for a defensin-non-defensin peptide combination is, therefore, termed "synergistic" because the potential for synergy is present even if synergy is not observed under all conditions. The synergy between a plant defensin and a peptide provides greater pathogen inhibition than can be obtained by either component acting alone, for at least some dosages. In some cases, one of the defensin or peptide is not measurably effective against a particular pathogen until combined with the other. Therefore, the present invention provides for increased protection of a host from pathogen infestation with reduced dependence on chemical pathogenicides or antibiotics. This means decreased input cost to the human and animal health system and plant growers, a broader spectrum of activity against pathogens and reduced potential for environmental damage or spread of antibiotic resistance. Hence, in relation to the latter, the selection pressure for development of pathogenicide-resistant pathogen strains is greatly reduced, which allows for an extended commercial life of the agents as well as reduced proliferation of resistant pathogens and reduced likelihood of emergence of multiple-resistant strains of pathogens.

"Pathogen inhibition" includes both pathogenicidic and pathogenostatic activity, as measured by reduction of pathogen growth (or loss of viability) compared to a control. Pathogen growth can be measured by many different methods known in the art depending on the pathogen. A commonly used method of measuring growth of a filamentous fungus, for example, entails germinating spores in a suitable growth medium, incubating for a time sufficient to achieve measurable growth, and measuring increased optical density in the culture after a specified incubation time. The optical density rises with increased growth. Typically, fungal growth is necessary for pathogenesis. Therefore, inhibition of pathogen growth provides a suitable indicator for protection from fungal disease, i.e. the greater the inhibition, the more effective the protection. Cell viability can be measured using commercial kits that rely on colorometric dyes such as MTT (3-[4,5-dimethylthiazol-2-yl]-2,5-diphenyltetrazolium bromide) or resazurin (7-Hydroxy-3H-phenoxazin-3-one 10-oxide) or by plating cells onto agar plates and counting the number of colony forming units that appear. Inhibition of insects can readily be achieved using feeding trials. Microbicidal activity can be measured on solid agar or in liquid culture.

"Preventing infection" in the present context, means that the human, animal or plant host treated with the combination of defensin and, non-defensin peptide agents, avoids pathogen infection or disease symptoms or all of the above, or exhibit reduced or minimized or less frequent pathogen infection or disease symptoms or all of the above, that are the natural outcome of the host-pathogen interactions when compared to the host not exposed to the defensin or peptide or both. That is to say, pathogens are prevented or reduced from causing disease and/or the associated disease symptoms. Infection and/or symptoms are reduced by at least about 10%, 20%, 30%, 40%, 50, 60%, 70% or 80% or greater as compared to a host not so treated with the protocol taught herein. The percentage reduction can be determined by any convenient means appropriate to the host and pathogen.

Hence, the combined action of the defensin and peptide agents is to inhibit pathogen growth, replication, infection and/or maintenance, amongst other inhibitory activities and/or induces amelioration of symptoms of pathogen infection or infestation.

Plant protection (disease resistance or reduction) can be evaluated by methods known in the art. See, Uknes et al. (1993) *Molecular Plant Microbe Interaction* 6:680-685; Gorlach et al. (1996) *Plant Cell* 8:629-643; Alexander et al. (1993) *Proc Natl Acad Sci USA* 90:7327-7371. The skilled artisan will recognize that methods for determining plant infection and disease by a plant pathogen depends on the pathogen and plant being tested. Human and animal protection (disease prophylaxis or treatment) can initially be tested using in vitro laboratory assays (e.g. pathogen inhibition assays) followed by animal studies and eventually human clinical trials.

By "contacting" includes exposure of the pathogen to the combination of the defensin and non-defensin peptide following topical or systemic administration or application to the human or animal subject or topical application or expression in or on a plant or introduction of a combination of the agents to an environmental site. Contact may be with plant or cell extracts which contain the defensin or peptide naturally or which have been engineered to produce one or other of the defensin or peptide. Plant extracts include herbal formulations and extracts such as natural body washes and shampoos. Hence, the defensin and the peptide may be applied topically to a surface area on the human or animal subject or plant or they may be systemically administered to the human or animal subject or one or other or both may be expressed in a plant genetically modified to produce the defensin and/or the peptide. Alternatively, in relation to plants, one of a defensin or peptide may be topically applied to the plant and the other of the defensin or peptide may be expressed by a plant genetically engineered to produce the defensin or peptide. Alternatively, the level of expression of an endogenous defensin is elevated to a sufficient level so as to be effective in combination with an expressed peptide or an exogenously supplied peptide. Alternatively, the defensin and peptide are dispersed into an environmental site such as soil or the surface of an inanimate object (e.g. door handle). In an embodiment, a defensin may be supplied exogenously to a plant or plant seed even though that plant may produce the same defensin.

In an alternative embodiment, microorganisms or plant cells are genetically engineered to express one or other or both of the defensin and the peptide. Such microorganisms or a mixture of microorganisms or plant cells or extracts thereof are useful as seed coating compositions, root colonizing compositions and soil-decontaminating compositions which may be applied by spray or admixed to soil and the like.

In an embodiment, the defensin and the non-defensin peptide are formulated together such as in a topical formulation, hair or body washing solution, seed coat formulation, root formulation or a formulation suitable for systemic administration to the appropriate host. A microbial mixture expressing one or both of the defensin and/or peptide may also be applied. Topical formulations include an aqueous solution, liquid formulation, tonic, a wash, a spray, paint, a powder, a dispersant, an atomized formulation, douche, cream, ointment, lipstick, gel, sludge, paste, patch, impregnated bandage and the like. Plant extracts comprising one or other or both of the defensin and peptide are also contemplated herein including a plant extract to which one or other of the defensin or peptide is added.

Enabled herein is a formulation comprising a plant defensin or a functional natural or synthetic derivative or variant thereof and a non-defensin peptide for use in inhibiting growth or infestation of a pathogen in or on a human or animal subject or a plant.

Further enabled herein is a formulation comprising a plant defensin or a functional natural or synthetic derivative or variant thereof and a non-defensin peptide for use in inhibiting growth or infestation of a pathogen on a surface or in material or other environmental locale comprising a pathogen or having the potential to be contaminated by a pathogen. An environment locale includes soil, environment surrounding a plant root ball, and the surface of an inanimate object such as a door handle, floor surface and table surface.

In an embodiment, taught herein is a therapeutic kit comprising multiple compartments wherein a first compartment comprises a plant defensin or a functional natural or synthetic derivative or variant thereof, a second compartment comprises a non-defensin peptide and optionally a third or further compartment comprising excipients, carriers or diluents wherein in use the contents of the first and second compartments are admixed prior to or during application to a human or animal subject or a plant or a surface or material comprising a pathogen or having the potential to be contaminated by the pathogen. The kit may also contain microorganisms such as in freeze-dried form which are reconstituted prior to use. The microorganisms are engineered to express one or other or both of the defensin and/or the peptide. Alternatively, the kit comprises a cellular extract comprising the defensin and/or peptide.

Described and enabled herein is a defensin or a functional natural or synthetic derivative or variant thereof and a non-defensin peptide for use in inhibiting growth or infestation of a pathogen or contamination by a pathogen, the defensin and the peptide being used in combination so as to act in synergy.

Reference to a "plant defensin" includes a functional natural or synthetic derivative or variant thereof unless the context clearly indicates otherwise. Examples of suitable defensins contemplated herein include permeabilizing defensins, Solanaceous Class II defensins and functional natural or synthetic derivatives or variants thereof.

The defensins used herein may be referred to herein as "naturally occurring" defensin, a "modified" defensin, a "variant" defensin, a "mutated" defensin or a "chimeric" defensin, depending on its source.

In an embodiment, the permeabilizing defensin is a Class II Solanaceous defensin. In an embodiment, the defensin is modified at the loop region between the first β-strand (β-strand 1) and the α-helix at the N-terminal end portion of the defensin. In an embodiment, the loop region comprises the 6 amino acids N-terminal of the second invariant cysteine residue or its equivalent. This region is defined as "Loop1B". A Class II Solanaceous defensin is distinguished from other defensins by a relatively conserved C-terminal end portion of the mature domain. Reference to a "Class II Solanaceous defensin" includes any defensin having at least 70% amino acid sequence similarity to the C-terminal end portion of the NaD1 mature domain, the C-terminal portion of NaD1 comprising approximately 20 contiguous amino acid residues ending and including the most C-terminal invariant cysteine in the NaD1 mature domain (for example, SEQ ID NO:1). By "at least 70%" means at least 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100%.

In an embodiment, the Loop1B amino acid sequence in a Class II Solanaceous defensin is modified to the sequence $X_1 X_2 X_3 X_4 X_5 X_6$ (SEQ ID NO:2) wherein:

$X_1$ is A, R, N, D, C, Q, E, G, H, I, L, K, M, F, P, S, T, W, Y or V or a naturally occurring modified form thereof;

$X_2$ is A, R, N, D, C, Q, E, G, H, I, L, K, M, F, P, S, T, W, Y or V or a naturally occurring modified form thereof;

$X_3$ is A, R, N, D, C, Q, E, G, H, I, L, K, M, F, P, S, T, W, Y or V or a naturally occurring modified form thereof;

$X_4$ is A, R, N, D, C, Q, E, G, H, I, L, K, M, F, P, S, T, W, Y or V or a naturally occurring modified form thereof;

$X_5$ is A, R, N, D, C, Q, E, G, H, I, L, K, M, F, P, S, T, W, Y or V or a naturally occurring modified form thereof; and/or $X_6$ is A, R, N, D, C, Q, E, G, H, I, L, K, M, F, P, S, T, W, Y or V or a naturally occurring modified form thereof;

using single letter amino acid nomenclature, wherein the amino acid sequence $X_1 X_2 X_3 X_4 X_5 X_6$ does not correspond to an amino acid sequence of the Loop1B region from the Class II Solanaceous defensin prior to modification.

In an embodiment, the Loop1B sequence in a Class II Solanaceous defensin is modified to the sequence $X_1 X_2 X_3 X_4 X_5 X_6$ (SEQ ID NO:3) wherein:

$X_1$ is N, G, D, H, K, A, E, Q, T, P, L, M, S, or R;
$X_2$ is K, R, G, H, L, N, F, I, S, T or Y;
$X_3$ is W, Y, H, L, G, F or P;
$X_4$ is P, K, S, R, H, T, E, V, N, Q, D or G;
$X_5$ is S, K, Y, F, G or H; and/or
$X_6$ is P, V, L, T, A, F, N, K, R, M, G, H, I or Y;

wherein the amino acid sequence $X_1 X_2 X_3 X_4 X_5 X_6$ does not correspond to an amino acid sequence of the Loop1B region from the Class II Solanaceous defensin prior to modification.

In an embodiment, the Loop1B sequence in a Class II Solanaceous defensin is modified to the sequence $X_1 X_2 X_3 X_4 X_5 X_6$ (SEQ ID NO:4) wherein:

$X_1$ is N, H, Q, D, K or E;
$X_2$ is R, H, T, K or G;
$X_3$ is F, H, Y or W;
$X_4$ is P, K, S or R;
$X_5$ is G or F; and
$X_6$ is P, V, I or N;

wherein the amino acid sequence $X_1 X_2 X_3 X_4 X_5 X_6$ does not correspond to an amino acid sequence of the Loop1B region from the Class II Solanaceous defensin prior to modification.

Reference to "$X_1 X_2 X_3 X_4 X_5 X_6$" means 6 contiguous amino acid residues corresponding to a Loop1B region.

In an embodiment, the artificially created or modified defensin comprises the amino acid sequence as set forth in SEQ ID NO:5. In this sequence, the Loop1B region is defined as $X_1 X_2 X_3 X_4 X_5 X_6$ wherein:

$X_1$ is an amino acid selected from the list consisting of: L, F, S, I, A, H, Y, Q, D, K or G;

$X_2$ is an amino acid selected from the list consisting of: S, V, F, I, K, L, A, P, N, T, R, H or G;

$X_3$ is an amino acid selected from the list consisting of: A, F, W, N, I, S, Y, P, L or H;

$X_4$ is an amino acid selected from the list consisting of: K, G, E, R, A, P, F, Q, V or S;

$X_5$ is an amino acid selected from the list consisting of: M, G, K, D, S, Y, P, E, N or F; and $X_6$ is an amino acid selected from the list consisting of: V, T, M, S, W, A, P, G, E, K, L, H, I or N.

In an embodiment, the artificially created or modified defensin comprises the amino acid sequence as set forth in SEQ ID NO:6. In this sequence, the Loop1B region is defined as $X_1 X_2 X_3 X_4 X_5 X_6$ wherein:

$X_1$ is an amino acid selected from the list consisting of: N, H, Q, D, K or E;

$X_2$ is an amino acid selected from the list consisting of: R, H, T, K or G;

$X_3$ is an amino acid selected from the list consisting of: F, H, Y or W;

$X_4$ is an amino acid selected from the list consisting of: P, K, S or R;

$X_5$ is an amino acid selected from the list consisting of: G or F; and $X_6$ is an amino acid selected from the list consisting of: P, V, I or N.

In the case of NaD1, a Class II Solanaceous defensin, the Loop1B amino acid sequence is NTFPGI (SEQ ID NO:7). Consequently, the NTFPGI is modified such that N is replaced by one of A, R, D, C, Q, E, G, H, I, L, K, M, F, P, S, T, W, Y or V or a naturally occurring modified form thereof; the T is replaced by one of A, R, N, D, C, Q, E, G, H, I, L, K, M, F, P, S, W, Y or V or a naturally occurring modified form thereof; the F is replaced by one of A, R, N, D, C, Q, E, G, H, I, L, K, M, P, S, T, W, Y or V or a naturally occurring modified form thereof; the P is replaced by one of A, R, N, D, C, Q, E, G, H, I, L, K, M, F, S, T, W, Y or V or a naturally occurring modified form thereof; the G is replaced by one of A, R, N, D, C, Q, E, H, I, L, K, M, F, P, S, T, W, Y or V or a naturally occurring modified form thereof; and/or the I is replaced by one of A, R, N, D, C, Q, E, G, H, L, K, M, F, P, S, T, W, Y or V; with the proviso that the Loop1B amino acid sequence does not correspond to the Loop1B from NaD1. The Loop1B sequence may have a single amino acid change or 2 or 3 or 4 or 5 or all 6 amino acids may be altered.

The Class II Solanaceous defensin may be modified by any number of amino acid changes to the Loop1B region alone or in combination with other mutations. Other mutations include amino acid substitutions, additions and/or deletions. Mutations outside the Loop1B region may number from 1 to about 50. A "change" includes a graft of a Loop1B region from one defensin to replace a Class II Solanaceous defensin Loop1B region. The source may be a Class I defensin Loop1B or a Loop1B from another Class II defensin. These aspects are based on the proviso that the enhanced anti-pathogen activity of the combined use of the modified defensin and peptide against at least one plant or animal pathogen is maintained. In an embodiment, the anti-pathogen activity is enhanced relative to the Class II defensin prior to modification in terms of level or spectrum of activity, stability and/or permeabilization. In an embodiment, the anti-pathogen activity is enhanced relative to the peptide prior to modification of the Class II defensin in terms of level or spectrum of activity, stability and/or permeabilization.

Hence, included herein is the use of an artificially created defensin comprising a modified Class II Solanaceous defensin backbone wherein the loop region between β-strand 1 and the α-helix on the N-terminal end portion is modified by a single or multiple amino acid substitution, addition and/or deletion to generate a variant defensin which has anti-pathogen activity. In an embodiment, the loop region is Loop1B defined by the 6 amino acid residues N-terminal to the second invariant cysteine residue. Its equivalent region in any defensin is contemplated herein.

Examples of suitable defensins include NaD1, TPP3, PhD1, PhD1A, PhD2, FST, NoD173, HXL001 (SEQ ID NO:25), HXL002 (SEQ ID NO:26), HXL004 (SEQ ID NO:27), HXL007 (SEQ ID NO:28), HXL008 (SEQ ID NO:29), HXL012 (SEQ ID NO:32), HXL013 (SEQ ID NO:30), HXL015 (SEQ ID NO:31), HXL035 (SEQ ID NO:33) and HXL036 (SEQ ID NO:34). Examples of synthetic defensin variants include HXP4 (SEQ ID NO:8), HXP34 (SEQ ID NO:15) and HXP35 (SEQ ID NO:16). Other examples of variant defensins include HXP37 (SEQ ID NO:17), HXP58 (SEQ ID NO:18), HXP72 (SEQ ID NO:19), HXP91 (SEQ ID NO:20), HXP92 (SEQ ID NO:21), HXP95 (SEQ ID NO:22) and HXP107 (SEQ ID NO:23).

Taught herein is a method for inhibiting growth or infestation of a pathogen, the method comprising contacting the pathogen with an effective amount of a combination of a plant defensin selected from the list consisting of NaD1, TPP3, PhD1, PhD1A, PhD2, FST, NoD173, HXL001, HXL002, HXL004, HXL007, HXL008, HXL012, HXL013 HXL015, HXL035 and HXL036 or a variant or derivative of a defensin selected from the list consisting of HXP4, HXP34, HXP35, HXP37, HXP58, HXP72, HXP91, HXP92, HXP95 and HXP107 and a peptide having anti-pathogen properties, the combination of the defensin and the peptide being synergistic compared to the use of each alone at the same individual dose as used in the combination.

Reference to a “peptide having anti-pathogen properties” includes a peptide of from 4 to 100 amino acid residues including 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 amino acid residues in length or from 0.4 to 12 kD in size such as 0.4, 0.5, 0.6, 07, 0.8, 0.9, 1, 2, 3, 4, 5, 6, 7, 8, 9, 10, 11 or 12 kD.

The peptide is a peptide other than a plant defensin peptide and encompasses a 4 to 100 amino acid residue peptide or a 0.4 to 12 kD peptide characterized as being an α-helical peptide (e.g. an α-helical cathelicidin peptide), a peptide forming a hairpin stabilized by a disulfide bridge (e.g. α-hairpinins and β-hairpins), a peptide with extended conformation, a peptide enriched with specific amino acid residues and/or a peptide derived from a proteinase inhibitor. It is a non-plant defensin peptide which may or may not exhibit anti-pathogen activity on its own. Antimicrobial peptides belonging to the cathelicidin family are extremely diverse in both sequence and structure and can form α-helical, β-hairpin, or extended conformations. Cathelicidins are expressed as precursor proteins with an N-terminal prosequence. This sequence of approximately 100 amino acids is also related to cathelin, a cystatin-like protein. This cathelin-like domain is cleaved to release the mature cathelicidin peptide. α-Hairpinins are small (33-51 amino acids) peptides that are characterized by two CXXXC motifs separated by between 10 and 13 amino acids. The structure of α-hairpinins is characterized by two alpha helical regions, each containing one CXXC motif, with an intervening loop region. Two disulphide bonds are formed between the CXXXC motifs to form a stable hairpin structure.

An example of α-helical peptides include cathelicidin peptides derived from human or from a non-human primate or a rodent, porcine, bovine, caprine animal such as LL-37, BMAP28, SMAP29, PMAP23, mCRAMP, RK-31 and KS-30.

Examples of α-helical peptides include LL-37, SMAP29, BMAP28, mCRAMP, RK-31, KS-30 and CP-29.

Examples of β-hairpins include bactenecin, protegrin tachyplesins (e.g. tachyplesin II), androctonin, polyphemusins (e.g. polyphemusin (F12I), polyphemusin I and polyphemusin II), gomesin, thanatin and brevenins. Examples of α-hairpinins include peptides from plant sources including Sit_HPN_100A, EcAMP1, Osa_HPN_86B, Sbi_HPN_104C, Sbi_HPN_104I, Cil_HPN_14F, BWI-2c, BWI-2b, luffin P1, MBP-1, MiAMP2d, C2 and VhT1.

Examples of extended conformation peptides include indolicidin, Bac2A and EcAMP4A. These include synthetic hairpin peptides such as Bac2A and EcAMP4A where the disulfide bonds of a β-hairpin or α-hairpinin are removed by replacing the cysteine residues with alanine residues.

An example of a peptide enriched for specific amino acids is indolicidin.

Examples of a peptide derived from a proteinase inhibitor, when the proteinase inhibitor is cystatin, include SlCys9N (67-92), SlCys9N (77-110), HvCPI6 (75-99) and CC7 (71-104).

Some α-hairpinin and β-hairpin peptides show efficacy on their own against pathogens at a concentration higher than the concentration used in a combination with a plant defensin. A method for inhibiting growth or infection or infestation of a pathogen, the method comprising contacting the pathogen with an effective amount of α-hairpinin and β-hairpin or a functional natural or synthetic derivative or variant thereof at a concentration greater than the concentration required to inhibit growth or infection or infestation when used in combination with a plant defensin. In an embodiment, the pathogen is a fungal pathogen as defined herein. In an embodiment, the fungal pathogen is selected from the list consisting of *Fusarium* sp, *Colletotrichum* sp, *Saccharomyces* sp, *Candida* sp and *Trichophyton* sp. In an embodiment, the fungal pathogen is *Fusarium graminearum, Colletotrichum graminicola, Saccharomyces cerevisiae, Candida albicans* and *Trichophyton rubrum*. Examples of α-hairpinin and β-hairpin include but are not limited to CilHPN_14F, OsaHPN_86B, SitHPN_100A, SbiHPN_104C, SbiHPN_104I, EcAMP1, Androctonin and Polyphemusin I.

The peptide is not a defensin and is referred to as a non-defensin peptide or a non-plant defensin peptide. It may or may not on its own exhibit anti-pathogen properties. Peptides are available from standard commercial sources and include chemically synthesized peptides.

Taught herein is a method for inhibiting growth or infestation of a pathogen, the method comprising contacting the pathogen with an effective amount of combination of a plant defensin selected from the list consisting of NaD1, TPP3, PhD1, PhD1A, PhD2, FST, NoD173, HXL001, HXL002, HXL004, HXL007, HXL008, HXL012, HXL013 HXL015, HXL035 and HXL036 or a variant or derivative of a defensin selected from the list consisting of HXP4, HXP34, HXP35, HXP37, HXP58, HXP72, HXP91, HXP92, HXP95 and HXP107 and a non-defensin peptide selected from the list consisting of Sit_HPN_100A, EcAMP1, Osa_HPN_86B, Sbi_HPN_104C, Sbi_HPN_104I, Cil_HPN_14F, LL-37, SMAP29, BMAP28, mCRAMP, RK-31, KS-30, EcAMP4A, BWI-2c, BWI-2b, MBP-1, MiAMP2d, C2, VhT1, SlCys9N(67-92), SlCys9N(77-110), HvCPI6(75-99), CC7(71-104), bactenecin, Bac2A, indolicidin and CP-29 the combination of the defensin and the peptide being synergistic compared to the use of each alone at the same individual dose as used in the combination.

As indicated above, the pathogen is selected from a fungus and a microorganism.

Taught herein is a method for inhibiting growth or infestation of a fungal pathogen, the method comprising contacting the fungal pathogen with an effective amount of combination of a plant defensin selected from the list consisting of NaD1, TPP3, PhD1, PhD1A, PhD2, FST, NoD173, HXL001, HXL002, HXL004, HXL007, HXL008, HXL012, HXL013 HXL015, HXL035 and HXL036 or a variant or derivative of a defensin selected from the list consisting of HXP4, HXP34, HXP35, HXP37, HXP58, HXP72, HXP91, HXP92, HXP95 and HXP107 and a non-defensin peptide selected from the list consisting of Sit_HPN_100A, EcAMP1, Osa_HPN_86B, Sbi_HPN_104C, Sbi_HPN_104I, Cil_HPN_14F, LL-37, SMAP29, BMAP28, mCRAMP, RK-31, KS-30, EcAMP4A, BWI-2c, BWI-2b, MBP-1, MiAMP2d, C2, VhT1, SlCys9N(67-92), SlCys9N(77-110), HvCPI6(75-99), CC7(71-104), bactenecin, Bac2A, indolicidin and CP-29 the combination of the defensin and the peptide being synergistic compared to the use of each alone at the same individual dose as used in the combination.

Taught herein is a method for inhibiting growth or infestation of a microbial pathogen, the method comprising contacting the microbial pathogen with an effective amount of combination of a plant defensin selected from the list consisting of NaD1, TPP3, PhD1, PhD1A, PhD2, FST, NoD173, HXL001, HXL002, HXL004, HXL007, HXL008, HXL012, HXL013 HXL015, HXL035 and HXL036 or a variant or derivative of a defensin selected from the list consisting of HXP4, HXP34, HXP35, HXP37, HXP58, HXP72, HXP91, HXP92, HXP95 and HXP107 and a non-defensin peptide selected from the list consisting of Sit_HPN_100A, EcAMP1, Osa_HPN_86B, Sbi_HPN_104C, Sbi_HPN_104I, Cil_HPN_14F, LL-37, SMAP29, BMAP28, mCRAMP, RK-31, KS-30, EcAMP4A, BWI-2c, BWI-2b, MBP-1, MiAMP2d, C2, VhT1, SlCys9N (67-92), SlCys9N(77-110), HvCPI6(75-99), CC7(71-104), bactenecin, Bac2A, indolicidin and CP-29 the combination of the defensin and the peptide being synergistic compared to the use of each alone at the same individual dose as used in the combination.

The present method is useful in the treatment or prophylaxis of a subject having an infection or infestation by a pathogen or decontamination of material containing a pathogen. The term "subject" includes a human of any age or an animal such as a farm animal (e.g. sheep, pig, horse, cow, donkey, llama, alpaca or poultry bird (e.g. chicken, duck, turkey, pheasant, peacock)), companion animal (e.g. dog or cat), laboratory test animal (e.g. mouse, rat, rabbit, guinea pig or hamster) or captive wild animal (e.g. kangaroo, Tasmanian devil or wild feline animal). A "human" or "animal" includes a part thereof such as fingers, toes, nails, eyes, ears, mouth, skin and scalp.

The subject also includes a plant such as a crop plant, ornamental plant, flowering plant or a plant considered native or indigenous to a particular country or region (e.g. a eucalypt). Reference to a "plant" includes a whole plant and parts thereof, including, but not limited to, shoots, vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit (the mature ovary), plant tissue (e.g. vascular tissue, ground tissue, and the like) and cells (e.g. guard cells, egg cells, and the like), and progeny of same. The plants that can be protected using the protocol of the present invention include higher and lower plants, including angiosperms (monocotyledonous and dicotyledonous plants), gymnosperms, ferns, horsetails, psilophytes, lycophytes, bryophytes, and multicellular algae. Plants which can be treated include any vascular plant, for example monocotyledons or dicotyledons or gymnosperms, including, but not limited to, alfalfa, apple, *Arabidopsis*, banana, barley, canola, castor bean, chrysanthemum, clover, cocoa, coffee, cotton, cottonseed, corn (maize), crambe, cranberry, cucumber, dendrobium, dioscorea, eucalyptus, fescue, flax, gladiolus, liliacea, linseed, millet, muskmelon, mustard, oat, oil palm, oilseed rape, papaya, peanut, pineapple, ornamental plants, *Phaseolus*, potato, rapeseed, rice, rye, ryegrass, safflower, sesame, sorghum, soybean, sugarbeet, sugarcane, sunflower, strawberry, tobacco, tomato, turfgrass, wheat and vegetable crops such as lettuce, celery, broccoli, cauliflower, cucurbits, onions (including garlic, shallots, leeks, and chives); fruit and nut trees, such as apple, pear, peach, orange, grapefruit, lemon, lime, almond, pecan, walnut, hazel; vines, such as grapes, kiwi, hops; fruit shrubs and brambles, such as raspberry, blackberry, gooseberry; forest trees, such as ash, pine, fir, maple, oak, chestnut, poplar; with alfalfa, canola, castor bean, corn, cotton, crambe, flax, linseed, mustard, oil palm, oilseed rape, peanut, potato, rice, safflower, sesame, soybean, sugarbeet, sugarcane, sunflower, tobacco, tomato, and wheat preferred. Plants which can be treated include any crop plant, for example, forage crop, oilseed crop, grain crop, fruit crop, vegetable crop, fiber crop, spice crop, nut crop, turf crop, sugar crop, beverage crop, and forest crop. The crop plant can be corn, soybean, wheat, cotton, alfalfa, canola, sugarbeet, rice, potato, tomato, onion, a legume, or a pea plant. In one aspect, reference to "plant" includes its progeny and other descendents. In an embodiment, plant seeds are protected from fungal or bacterial infection or infestation by the topical administration of a defensin and the peptide or via the use of microorganisms which express one or other or both of the defensin and/or peptide.

As indicated above, reference to a "pathogen" includes a fungus and a microorganism. A "microorganism" includes a bacterium. A "fungus" includes a yeast and a rust.

Reference to a "fungus" includes fungi which infect and are otherwise pathogens of human or animal subject or plants.

Animal including mammalian such as human fungal pathogens include species of *Alternaeria* spp, *Aspergillus* spp, *Candida* spp, *Fusarium* spp, *Trichophyton* spp, *Cryptococcus* spp, *Histoplasma* spp, *Microsporum* spp, *Penicillium* spp, *Pneumocystis* spp *Trichosporon* spp, *Scedosporium* spp, *Paeciliomyces* spp, *Acremonium* spp, *Stachybotrys* spp and Dermatiaceous molds. Specific animal, including mammalian and in particular human pathogens include *Alternaria alternata, Aspergillus fumigatus, Aspergillus niger, Aspergillus flavus, Aspergillus nidulans, Aspergillus paraciticus, Candida albicans, Candida dubliniensis, Candida famata, Candida glabrata, Candida guilliermondii, Candida haemulonii, Candida kefyr, Candida krusei, Candida lusitaniae, Candida norvegensis, Candida parapsilosis, Candida tropicalis, Candida viswanathii, Epidermophyton floccosum, Fusarium oxysporum, Fusarium solani, Fusarium monoliforme, Trychophyton rubrum, Trychophyton mentagrophytes, Trychophyton interdigitales, Trychophyton tonsurans, Cryptococcus neoformans, Cryptococcus gattii, Cryptococcus grubii, Microsporum canis, Microsporum gypseum, Penicillium marneffei, Tricosporon beigelii, Trichosporon asahii, Trichosporon inkin, Trichosporon asteroides, Trichosporon cutaneum, Trichosporon domesticum, Trichosporon mucoides, Trichosporon ovoides, Trichosporon pullulans, Trichosporon loubieri, Trichosporon japonicum, Scedosporium apiospermum, Scedosporium prolificans, Paecilomyces variotii, Paecilomyces lilacinus, Acremonium strictum, Cladophialophora bantiana, Wangiella dermatitidis, Ramichloridium obovoideum, Chaetomium atrobrunneum, Dactlaria gallopavum, Bipolaris* spp, *Exserohilum rostratum* as well as *Absidia corymbifera, Apophysomyces elegans, Mucor indicus, Rhizomucor pusillus, Rhizopus oryzae, Cunninghamella bertholletiae, Cokeromyces recurvatus, Saksenaea vasiformis, Syncephalastrum racemosum, Basidiobolus ranarum, Conidiobolus coronatus, Conidiobolus incongruus, Blastomyces dermatitidis, Coccidioides immitis, Coccidioides posadasii, Histoplasma capsulatum, Paracoccidioides brasiliensis, Pseudallescheria boydii* and *Sporothrix schenckii*.

Specific pathogens for the major crops include: Corn: *Gibberella zeae (Fusarium graminearum), Colletotrichum graminicola, Stenocarpella maydi (Diplodia maydis), Fusarium moniliforme* var. *subglutinans, Fusarium verticilloides, Bipolaris maydis* O, T (*Cochliobolis heterostrophus*), *Exserohilum turcicum* I, II and III, *Cercospora zeae-maydis, Pythium irregulare, Pythium debaryanum, Pythium graminicola, Pythium splendens, Pythium ultimum, Pythium aphanidermatum, Aspergillus* spp, *Aspergillus flavus, Helminthosporium carbonum* I, II and III (*Cochliobolus carbonum*), *Helminthosporium pedicellatum, Physoderma maydis, Phyllosticta maydis, Kabatiella maydis, Cercospora sorghi, Ustilago maydis, Ustilago zeae, Puccinia sorghi, Puccinia polysora, Macrophomina phaseolina, Penicillium oxalicum, Nigrospora oryzae, Cladosporium herbarium, Curvularia lunata, Curvularia inaequalis, Curvularia pallescens, Trichoderma viride, Claviceps sorghi, Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporum maydis, Cephalosporum acremonium*; Soybeans: *Fusarium virgululiforme, Fusarium solani, Sclerotinia sclerotiorum, Fusarium oxysporum, Fusarium tucumaniae, Phakopsora pachyrhizi Phytophthora megasperma* f.sp. *glycinea, Phytophthora sojae, Macrophomina phaseolina, Rhizoctonia solani, Sclerotinia sclerotiorum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotrichum truncatum*), *Corynespora cassiicola, Septoria glycines, Phyllosticta sojicola, Alternaria alternata, Microsphaera diffusa, Fusarium semitectum, Phialophora gregata, Glomerella glycines, Pythium aphanidermatum, Pythium ultimum, Pythium debaryanum*; Canola: *Albugo candida, Alternaria brassicae, Leptosphaeria maculans, Rhizoctonia solani, Sclerotinia sclerotiorum, Mycosphaerella brassicicola, Pythium ultimum, Peronospora parasitica, Fusarium oxysporum, Fusarium avenaceum, Fusarium*

*roseum, Alternaria alternata*; Cotton: *Fusarium oxysporum* f.sp. *vasinfectum, Verticillium dahliae, Thielaviopsis basicola, Alternaria macrospora, Cercospora gossypina, Phoma exigua (Ascochyta gossypii), Pythium* spp *Rhizoctonia solani, Puccinia scheddardii, Puccinia cacabata, Phymatotrichopsis omnivore*; Canola: *Leptosphaeria maculans, Sclerotinia sclerotiorum, Alternaria brassicae, Alternaria brasicicola, Plasmodiophora brassicae, Rhizoctonia solani, Fusarium* spp, *Pythium* spp, *Phytophthora* spp, *Alternaria* spp, *Peronospora parasitica, Mycosphaerella capsellae (Pseudocercosporella capsellae), Albugo candida, Phytophtohora megasperma* var. *megasperma, Botrytis cinerea, Erysiphe cruciferarum*; Wheat: *Cochliobolus sativus, Drechslera wirreganensis, Zymoseptoria tritici (Mycosphaerella graminicola), Phaeosphaeria avenaria* f.sp. *triticea, Phaeosphaeria nodorum, Blumeria graminis* f.sp. *tritici, Urocystis agropyri, Alternaria alternata, Cladosporium herbarum, Fusarium graminearum, Fusarium avenaceum, Fusarium culmorum, Fusarium pseudograminearum, Ustilago tritici, Ascochyta tritici, Cephalosporium gramineum, Colletotrichum graminicola, Erysiphe graminis* f.sp. *tritici, Puccinia graminis* f.sp. *tritici, Puccinia recondita* f.sp. *tritici, Puccinia striiformis, Puccinia triticina, Sclerophthora macrospora, Urocystis agropyri, Pyrenophora tritici-repentis, Pyrenophora semeniperda, Phaeosphaeria nodorum, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium* spp, *Pythium aphanidermatum, Pythium arrhenomannes, Pythium gramicola, Pythium ultimum, Bipolaris sorokiniana, Claviceps purpurea, Tapesia yallundae, Tilletia tritici, Tilletia laevis, Tilletia caries, Tilletia indica, Ustilago tritici, Wojnowicia graminis, Cochliobolus sativus*; Sorghum: *Exserohilum turcicum, Colletotrichum sublineolum, Cercospora sorghi, Gloeocercospora sorghi, Ascochyta sorghina, Puccinia purpurea, Macrophomina phaseolina, Perconia circinata, Fusarium moniliforme, Alternaria alternata, Bipolaris sorghicola, Helminthosporium sorghicola, Curvularia lunata, Phoma insidiosa, Ramulispora sorghi, Ramulispora sorghicola, Phyllachara saccari, Sporisorium reilianum (Sphacelotheca reiliana), Sphacelotheca cruenta, Sporisorium sorghi, Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*; Sunflower: *Plasmopara halstedii, Sclerotinia sclerotiorum, Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthe, Verticillium dahliae, Cephalosporum acremonium, Phytophthora cryptogea, Albugo tragopogonis*; Alfalfa: *Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Verticillium albo-atrum, Aphanomyces euteiches, Stemphylium herbarum, Stemphylium alfalfae, Colletotrichum trifolii, Leptosphaerulina briosiana, Uromyces striatus, Sclerotinia trifoliorum, Stagonospora meliloti, Stemphylium botryosum* and *Leptotrichila medicaginis.*

In an embodiment, fungal pathogens in corn include *Fusarium graminearum, Colletotrichum graminicola, Stenocarpella maydis, Fusarium verticilloides, Cochliobolis heterostrophus, Exserohilum turcicum, Cercospora zeamaydis.*

In an embodiment, fungal pathogens in soybean include *Fusarium virguliforme, Fusarium solanai, Sclerotinia sclerotiorum, Fusarium oxysporum, Fusarium tucumaniae, Phakopsora pachirhizi.*

In an embodiment, fungal pathogens of wheat include *Zymoseptoria tritici, Fusarium graminearum, Puccinia graminis* f.sp *tritici, Puccinia recondite* f.sp *tritici, Pyrenophora tritici-repentis.*

Reference to a "fungus" also includes oomycetes such as *Pythium* spp and *Phytophthora* spp. The term "fungus" also encompasses a rust.

Bacterial pathogens include *Xanthomonas* spp and *Pseudomonas* spp. Other microorganisms include *Phytoplasma* spp and *Spiroplasma* spp. Other microorganisms include *Staphylococcus* spp, *Streptococcus* ssp, *Salmonella* spp, *Proteus* spp, *E. coli* spp, *Mycobaterium* spp and *Mycoplasma* spp.

The instant disclosure further teaches nucleic acid molecules encoding the defensin or its derivative or variant and/or the non-defensin peptide. The nucleic acid molecule may be in an isolated form or part of a vector including an expression or transfer vector suitable for use in plant cells, microbial cells and non-human animal cells. Reference to a "vector" includes a multi-gene expression vector (MGEV) such as described by PCT/AU02/00123.

In accordance with the latter aspect, there is provided a multigene expression vehicle (MGEV) comprising a polynucleotide having 2 to 8 domain segments each domain encoding a functional protein, each domain being joined to the next in a linear sequence by a linker segment, the domain and segments all being in the same reading frame, and wherein at least one of the domains is a permeabilizing defensin such as a Class II Solanaceous defensin or a modified form thereof as herein described. In an embodiment, at least one other domain is a non-defensin peptide as herein described. In an embodiment, at least one domain is the defensin and at least one other domain is the peptide.

The nucleic acid sequence encoding the defensin and/or the peptide may be incorporated into a DNA construct or vector in combination with suitable regulatory sequences (promoter, terminator, transit peptide, etc). The nucleic acid may also be operably linked to a heterologous promoter. For some applications, the nucleic acid sequence encoding the defensin and/or peptide may be inserted within a coding region expressing another protein to form a defensin and/or peptide fusion protein or may be used to replace a domain of a protein to give that protein anti-pathogen activity. The nucleic acid sequence may be placed under the control of a homologous or heterologous promoter which may be a constitutive or an inducible promoter (stimulated by, for example, environmental conditions, presence of a pathogen, presence of a chemical). The transit peptide may be homologous or heterologous to the defensin and is chosen to ensure secretion to the desired organelle or to the extracellular space. The transit peptide may be naturally associated with a particular defensin. Such a DNA construct may be cloned or transformed into a biological system which allows expression of the encoded modified defensin or an active part of the defensin. Suitable biological systems include microorganisms (for example, the *Pichia pastoris* expression system, *Escherichia coli, Pseudomonas*, endophytes such as *Clavibacter xyii* subsp. *cynodontis* (Cxc); yeast; viruses; bacteriophages; etc), cultured cells (such as insect cells, mammalian cells) and plants. In some cases, the expressed defensin is subsequently extracted and isolated for use. In other cases, microbial cells expressing one or other or both of the defensin and/or peptide are applied to the plant or to the region around the roots or to seeds. In an embodiment, one of the defensin or peptide is produced by the microorganism and the other is topically applied. In an embodiment, one type of microorganism produces both the defensin and the peptide. In an embodiment, two different microorganisms each produces one or other of the defensin or peptide.

The combination of the defensin and peptide taught herein is useful for combating pathogen diseases or infection in humans, animals or plants as well as facilitating decontamination of environmental locale. Hence, the subject specification teaches a protocol for the treatment, prophylaxis or decontamination of pathogens. The protocol has human, veterinary, horticultural and/or agricultural applications. Further provided is a process of combating pathogens whereby they are exposed to the combination of a defensin and a peptide herein described. One or both of the defensins and/or peptide may be used in the form of a composition.

Another aspect taught herein is a composition comprising a plant defensin or a functional natural or synthetic derivative or variant thereof and a non-defensin peptide together with one or more pharmaceutically or veterinary or horticultural acceptable carriers, diluents or excipients. In another embodiment, two compositions are used, one comprising the defensin and another the non-defensin peptide. In an embodiment, the composition is in the form of a spray, mist, micro- or nano-particles, an aqueous solution, a wash, a tonic, a dispersant, an atomized formulation, douche, lipstick, sludge, powder, cream, ointment, gel, patch, impregnated bandage, liquid, formulation, paint or other suitable distribution medium including topical or systemic forms of the composition. By "systemic form" includes a form suitable or oral, intravenous intra peripheral, subcutaneous, intrathecal, intracranial, vaginal or rectal administration.

For pharmaceutical applications, the defensin and/or peptide may be used as a pathogenicide or a pathogenostatic agent to treat mammalian infections (for example, to combat yeasts such as *Candida*). Useful applications include powders, drops and ointments for fungal infection of the toes, feet, hands, nails, eyes, ears, mouth and scalp.

The defensin and peptide according to the present disclosure may also be used as a preservative (for example, as a food additive) or as part of a soil or growth medium preparation program or to assist in decontaminating the surface of inanimate objects such as door handles and table surfaces.

For agricultural applications, the modified defensin may be used to improve the disease-resistance or disease-tolerance of crops either during the life of the plant or for post-harvest crop protection. Growth, division, activity or infection or infestation potential of pathogens exposed to the combination of the defensin and the peptide is inhibited. The modified defensin may eradicate a pathogen already established on the plant or may protect the plant from future pathogen attack.

Exposure of a plant pathogen to the defensin and peptide may be achieved in various ways, for example:
(a) The agents may be applied to plant parts or to the soil or other growth medium surrounding the roots of the plants or to the seed of the plant before it is sown using standard agricultural techniques (such as spraying). The agents may have been chemically synthesized or extracted from microorganisms or plants or microorganisms genetically modified to express one or both of the defensin and/or peptide. The agents may be applied to plants or to the plant growth medium in the form of a composition comprising the defensin and the peptide in admixture with a solid or liquid diluent and optionally various adjuvants such as surface-active agents. Solid compositions may be in the form of dispersible powders, granules, or grains.
(b) A composition comprising a microorganism genetically modified to express the defensin and/or peptide may be applied to a plant or seed or the soil in which a plant grows.
(c) An endophyte genetically modified to express the defensin and/or peptide may be introduced into the plant tissue (for example, via a seed treatment process). An endophyte is defined as a microorganism having the ability to enter into non-pathogenic endosymbiotic relationships with a plant host. A method of endophyte-enhanced protection of plants has been described in a series of patent applications by Crop Genetics International Corporation (for example, International Application Publication Number WO90/13224, European Patent Publication Number EP-125468-B1, International Application Publication Number WO91/10363, International Application Publication Number WO87/03303). The endophyte may be genetically modified to produce agricultural chemicals. International Patent Application Publication Number WO94/16076 (ZENECA Limited) describes the use of endophytes which have been genetically modified to express a plant-derived anti-fungal peptide.
(d) DNA encoding the defensin and/or peptide may be introduced into the plant genome so that the peptide is expressed within the plant body (the DNA may be cDNA, genomic DNA or DNA manufactured using a standard nucleic acid synthesizer).

For compositions comprising the defensin and/or peptide described herein, generally include a carrier, excipient, diluent, preservative, stabilizer and/or a solid or liquid additive. Plant extracts comprising one or other or both of the defensin and/or peptides may also be used in a formulation such as a body wash or shampoo.

The composition may take a wide variety of forms depending on the intended method of administration. Generally, but not exclusively, topical compositions are used for human or animal subjects or a plant. In preparing the compositions, usual media may be employed such as, for example, water, glycols, oils, alcohols, preservatives and/or coloring agents. The compositions may take the form of a liquid preparation such as, for example, suspensions, elixirs and solutions. Carriers such as starches, sugars, microcrystalline cellulose, diluents, granulating agents, lubricants, binders, disintegrating agents and the like may also be used. The composition may also be in the form of a powder, capsule and tablet.

The defensin and the peptide may be administered directly to a plant or part thereof, to a seed or to the root system or soil or medium surrounding the root system or to the skin, hair or fur of an animal including a mammal such as a human.

When administered by aerosol or spray, the compositions are prepared according to techniques well-known in the art of agricultural and pharmaceutical formulation and may be prepared as solutions in saline, employing benzyl alcohol or other suitable preservatives, absorption promoters to enhance bioavailability, fluorocarbons and/or other solubilizing or dispersing agents known in the art.

The effective dosage of the defensin and peptide may vary depending on the particular combination employed, the mode of administration, the pathogen being treated and the severity of the pathogen infestation. Thus, the dosage regimen utilizing the defensin and peptide is selected in accordance with a variety of factors including type, species, age, weight, sex and medical condition of the plant or subject; the severity of the condition to be treated; the route of administration; and the particular defensin thereof employed. A horticulturist, physician, clinician or veterinarian of ordinary skill can readily determine and prescribe the effective amount of the defensin required to prevent, counter or arrest the progress of pathogen infestation. Slow release formulations are also contemplated herein.

Dragee cores are provided with suitable coatings. For this purpose, concentrated sugar solutions may be used, which may optionally contain gum arabic, talc, polyvinyl pyrrolidone, carbopol gel, polyethylene glycol and/or titanium dioxide, lacquer solutions, and suitable organic solvents or solvent mixtures. Dyestuffs or pigments may be added to the tablets or dragee coatings for identification or to characterize different combinations of active compound doses.

Defensin-non-defensin peptide preparations include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

The defensin-non-defensin peptide composition or expression vector encoding same may also comprise another anti-pathogen substance such as another defensin or an anti-pathogen protein or peptide, or a chemical pathogenicide or a proteinase inhibitor or precursor from thereof.

Another aspect taught herein includes a protocol or method for treating or preventing a plant infested with a pathogen, the protocol or method comprising applying to the plant or part thereof such as plant seeds or to the soil or growth support medium around the plant an anti-pathogen effective amount of a composition comprising a plant defensin and a non-defensin peptide as described herein, alone or together with another anti-pathogen agent.

Another aspect provides a protocol or method for treating or preventing an animal including a mammalian such as a human subject infected or infested with a pathogen, the protocol or method comprising applying to the subject an anti-pathogen effective amount of a composition comprising the plant defensin and a non-defensin peptide as described herein.

Another aspect provides a protocol or method for decontaminating an environmental locale infested with a pathogen, the protocol or method comprising applying to the locale an anti-pathogen effective amount of a composition comprising the plant defensin and a non-defensin peptide as described herein.

In another embodiment, microorganisms genetically modified to express one or other or both of the defensin and/or peptide are applied to the plant, seed, roots or to the human or animal.

The term "applying" includes contacting and exposing.

In a further embodiment, plant cells may be transformed with recombinant DNA constructs according to a variety of known methods (*Agrobacterium* Ti plasmids, electroporation, microinjection, microprojectile gun, etc). The transformed cells may in suitable cases be regenerated into whole plants in which the new nuclear material is stably incorporated into the genome. Both transformed monocotyledonous and dicotyledonous plants may be obtained in this way, although the latter are usually regenerated more easily. Some of the progeny of these primary transformants inherit the recombinant DNA encoding the anti-pathogen defensin and peptide combination.

The present disclosure further provides a plant having improved resistance to a pathogen and containing recombinant DNA which expresses a plant defensin and a non-defensin peptide. Such a plant may be used as a parent in standard plant breeding crosses to develop hybrids and lines having pathogen including fungal resistance. Alternatively, the plant may express a heterologous defensin or elevated expression of an endogenous defensin. In use, the peptide is exogenously supplied to such a plant. In another alternative, the plant expresses the peptide and a defensin is exogenously supplied. Hence, the present disclosure extends to transgenic plants and their progeny. In yet another embodiment, the defensin and/or the peptide is/are expressed by microorganisms exogenously supplied to the target. When a defensin is applied topically to a plant or plant seed, the plant itself may nevertheless produce that defensin naturally.

Recombinant DNA is DNA, generally heterologous, which has been introduced into the plant or its ancestors by transformation. The recombinant DNA encodes the defensin and the peptide expressed for delivery to a site of pathogen attack (such as the leaves).

Where the present defensin and non-defensin peptide are expressed within a transgenic plant or its progeny, the pathogen is exposed to the defensin and peptide at the site of or remote to the site of pathogen attack on the plant. In an embodiment, by use of appropriate gene regulatory sequences, the defensin may be produced in vivo when and where it will be most effective. For example, the defensin and peptide may be produced within parts of the plant where it is not normally expressed in quantity but where disease resistance is important (such as in the leaves).

Examples of genetically modified plants which may be produced include field crops, cereals, fruit and vegetables such as: corn, soybean, sorghum, wheat, barley, maize, cotton, canola, rice, abaca, alfalfa, almond, apple, asparagus, banana, bean-phaseolus, blackberry, broad bean, canola, cashew, cassava, chick pea, citrus, coconut, coffee, fig, flax, grapes, groundnut, hemp, lavender, mushroom, olive, onion, pea, peanut, pear, pearl millet, potato, rapeseed, ryegrass, strawberry, sugar beet, sugarcane, sunflower, sweetpotato, taro, tea, tobacco, tomato, triticale, truffle and yam.

A pathogen may be any pathogen growing on, in or near the plant. In this context, resistance includes an enhanced tolerance to a pathogen when compared to a wild-type plant. Resistance may vary from a slight increase in tolerance to the effects of the pathogen (where the pathogen in partially inhibited) to total resistance so that the plant is unaffected by the presence of pathogen (where the pathogen is severely inhibited or killed). An increased level of resistance against a particular pathogen or resistance against a wider spectrum of pathogens may both constitute an improvement in resistance. Transgenic plants (or plants derived therefrom) showing improved resistance are selected following plant transformation or subsequent crossing.

The present disclosure provides a method for generating a genetically modified plant or its progeny which exhibit anti-pathogen activity, the method comprising creating a plant which comprises cells which express nucleic acids encoding a plant defensin and a non-defensin peptide, as described herein, the level of expression sufficient for the defensin and peptide to exhibit a synergistic protective effect against a plant pathogen.

Provided herein is a method for generating a plant exhibiting anti-pathogen properties, the method comprising creating a genetically modified plant or its progeny which comprises cells which express a plant defensin and a non-defensin peptide. Such a plant has reduced risk of promoting resistance by pathogens.

The present defensin and peptide may be manufactured based on its amino acid sequence using standard stepwise addition of one or more amino acid residues using, for example, a peptide or protein synthesizer. Alternatively, the defensin and peptide may be made by recombinant means.

As indicated above, the combination of the defensin and peptide exhibits improved or enhanced anti-pathogen activity.

Still another aspect provides a method for reducing or controlling pathogen infection or infestation on or in a human or animal subject the method comprising topically applying a combination of a plant defensin and non-defensin peptide to a potentially infected surface region on the human or animal. Hence, animal and in particular mammalian such as human anti-pathogen medicaments are contemplated herein. In an embodiment, the medicament is in the form of a powder, spray, atomizer, nanoparticle, gel, paste, impregnated bandage, paint, aerosol, drench or other liquid. The anti-pathogen formulation may also be a slow release composition. The formulation may be used to treat an infected subject or as a preventative.

Another embodiment disclosed herein is a method for identifying a defensin which enhances or induces anti-pathogen activity of a peptide. Conveniently, the assay is conducted on fungal cells, however, cells of other species may be employed. The method entails measuring the ability of a defensin to permit entry into a fungal cell of a permeability indicator compound. A suitable permeabilization indicator compound is one whose location, whether intracellular or extracellular, can be detected. Under normal conditions, the indicator compound remains extracellular and does not freely pass through the cell wall and membrane. In the presence of a permeabilizing defensin the indicator compound can be detected inside the cell of a given fungus within 2 hours. If a defensin being tested (a test defensin) is found to increase permeability of a given fungus by increasing the intracellular amount of the indicator compound, when present with the fungus, that defensin is thereby identified as one that enhances or induces antifungal activity of a peptide, when the defensin and peptide are combined in the presence of the fungus. It is also proposed that the same defensin is useful enhancing or inducing the anti-pathogen properties of peptides in other pathogens such as microorganisms.

A suitable permeability indicator compound is a nucleic acid stain such as a green nucleic acid stain or a blue nucleic acid stain. The method of identifying a defensin that enhances peptide efficacy is not limited to the use of a nucleic acid stain, but can be carried out with any use of any permeability indicator compound that yields similar permeability data when tested with a defensin. A relative permeability index (RPI) is herein defined wherein the degree of permeabilization of a fungal strain induced by a defined concentration of a given defensin is addressed, relative to a value of 1.0 for NaD1 at the same concentration. Synergy may be expressed as a synergy scale. In an embodiment, a value of up to 14 represents no significant synergy such as 0, 1, 2, 3, 4, 5, 6, 7, 8, 9, 10, 11, 12, 13 or 14; a value of from 15 up to 29 represents low synergy such as 15, 16, 17, 18, 19, 20, 21, 22, 23, 24, 25, 26, 27, 28 or 29; a value of from 30 to 60 represents medium synergy such as 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60; a value greater than 60 represents a high degree of synergy. By "greater than 60" includes from 61 to 100 including 61, 70, 80, 90 and 100 and any value in between.

The described method is carried out using methods described below, or with adaptations that would be understood by one skilled in the art as being equivalent. The steps of the method include: combining a fungus with a permeability indicator compound in the presence of, and separately, as a control, in the absence of, a test defensin; then comparing any detectable intracellular amounts of the permeability indicator compound in the fungus in the presence and in the absence of the test defensin. If the effect of presence of the test defensin is such that an increased amount of intracellular indicator compound is detected in the fungus within 2 hours, compared to the control, the test defensin is identified as one which can enhance the efficacy of a non-plant defensin peptide the defensin and the fungicide are combined in the presence of the fungus. A plant defensin identified by the method just described will be understood to be useful as a defensin component of the system for protecting a plant from fungus disease as disclosed herein, whether or not the defensin is known to have anti-fungal activity.

Once a permeabilizing defensin is identified together with the concentration range providing optimal permeabilization, it is tested with different combinations of peptides against selected pathogens.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements. The present disclosure illustratively described herein suitably may be practiced in the absence of any element or elements, limitation or limitations which is not specifically disclosed herein.

When a Markush group or other grouping is used herein, all individual members of the group and all combinations and subcombinations possible of the group are intended to be individually included in the disclosure.

When a range is recited herein, it is intended that all subranges within the stated range, and all integer values within the stated range, are intended, as if each subrange and integer value was recited.

EXAMPLES

Aspects disclosed and enabled herein are now described in the following non-limiting Example.

Methods

Purification of Defensins from *Pichia Pastoris*

A single pPINK-defensin or pPIC9-defensin *P. pastoris* (PichiaPink or GS115 Trademark) strain 1 colony is used to inoculate 25 mL of BMG medium (described in the Invitrogen *Pichia* Expression Manual) in a 250 mL flask and that is incubated over for 2-3 days in a 30° C. shaking incubator (140 rpm). The culture is used to inoculate 200 mL of BMG in a 1 L baffled flask which is placed in a 30° C. shaking incubator (140 rpm) overnight. The cells are harvested by centrifugation (1,500×g, 10 min, 4° C.) and resuspended into 1 L of BMM medium in a 5 L baffled flask and incubated in a 28° C. shaking incubator for 3 days. The cultures are induced at t=24 and 48 h through the addition of 6 ml of 100% methanol. The expression medium is separated from cells by centrifugation (6000 rpm, 20 minutes). The medium is adjusted to pH 3.0 before it is applied to an SP Sepharose column (1 cm×1 cm, Amersham Biosciences) pre-equilibrated with 100 mM potassium phosphate buffer, pH 6.0. The column is then washed with 10 column volumes of 100 mM potassium phosphate buffer, pH 6.0 and bound protein is eluted in 10×10 mL of 100 mM potassium phosphate buffer containing either 500 mM or 1M NaCl. A small volume of each fraction (10 µL) is analysed using a dot blot and protein-containing fractions pooled. The proteins are concentrated down to 1 mL using a centrifugal column and washed 5× using sterile milli Q ultrapure water. The protein concentration of *Pichia*-expressed defensin is determined using the bicinchoninic acid (BCA) protein assay (Pierce Chemical Co.) with bovine serum albumin (BSA) as the protein standard.

Non-Defensin Peptides

Most of the non-defensin peptides were obtained from commercial sources. Generally, the peptides are chemically synthesized using standard peptide synthesizing machines and protocols.

EcAMP1 was produced recombinantly. DNA encoding the mature domain of the α-hairpinin EcAMP1 was ordered from Genscript. The DNA was excised from the pUC57 vector using Sac II and Sac I, extracted from agarose gels using the Perfectprep kit (Eppendorf) and ligated into pHUE which was then used to transform TOP10 *E. coli* cells. Plasmid DNA was isolated and then used to transform *E. coli* Rosetta-Gami B cells.

Single colonies of *E. coli* Rosetta-Gami B were used to inoculate 2YT media (10 mL, 16 g/L tryptone, 10 g/L yeast extract, 5 g/L NaCl) containing ampicillin (0.1 mg/mL), chloramphenicol (0.34 mg/mL), tetracycline (0.1 mg/mL) and kanamycin (0.015 mg/mL) and grown overnight with shaking at 37° C. This culture was used to inoculate 2YT media (500 mL) containing ampicillin (0.1 mg/mL), chloramphenicol (0.34 mg/mL), tetracycline (0.1 mg/mL) and kanamycin (0.015 mg/mL) which was then grown for 4 hours to an optical density (600 nm) of ~1.0. IPTG was then added (0.5 mM final concentration) and the culture grown for a further 16 hours at 16° C. Cells were harvested by centrifugation (4,000 g at 4° C. for 20 minutes), resuspended in native lysis buffer (20 mL per liter cell culture, 100 mM Tris-C1, 1M NaCl, 20 mM pH 8.0) and frozen at −80° C. Cells were then thawed and treated with lysozyme (5 mg per 25 mL resuspended cells) for 20 minutes at 4° C. DNase I (125 uL, 2 mg/mL in 20% glycerol, 75 mM NaCl) and $MgCl_2$ (125 uL, 1 M) were then added and the samples incubated at room temperature for 40 minutes on a rocking platform. The samples were then sonicated for 2×30 s on ice (80% power, Branson sonifier 450) and centrifuged (20,000 g at 4° C. for 30 minutes). The hexahistidine-tagged ubiquitin-fusion protein (His6-Ub-EcAMP1) was then purified from the protein extracts by immobilized metal affinity chromatography (IMAC) under native conditions using Ni-NTA resin (1.5 mL to ~25 mL native protein extract, Qiagen) according to the manufacturer's instructions. Recombinant proteins were eluted using elution buffer (100 mM Tris-Cl, 1 M NaCl, 500 mM imidazole pH 8.0). The imidazole was removed by applying the eluted protein to a prepacked Sephadex G50 gel filtration column (PD-10, Amersham) equilibrated with 50 mM Tris.Cl, 100 mM NaCl, pH 8.0.

The hexahistidine-tagged ubiquitin was cleaved from the recombinant proteins using the deubiquitylating enzyme 6H.Usp2-cc (Cantanzariti et al. 2004). The cleaved tag was removed by another round of IMAC with the deubiquitylated protease inhibitors as the unbound protein. This was then further purified by reversed-phase HPLC.

Permeabilization Assay

*Fusarium ozysporum* f. sp. *vasinfectum* (Fov) or *Fusarium graminearum* (Fgr) are grown in half-strength PDB from a starting concentration of $5 \times 10^4$ spores/mL for 18 hours at 25° C. Hyphal suspension (90 µL) is then transferred to black 96-well microtitre plates and incubated with SYTOX (Registered Trade Mark) green (0.5 µM) (a green nucleic fluorescent dye) for 10 minutes prior to the addition of 10 µL of peptide solution to give final protein concentration of 10 µM (Fov) or 5 µM (Fgr). SYTOX green uptake (indicating permeabilization) was quantified by measuring fluorescence using a microtitre plate reader (SpectraMax M5e; Molecular Devices) with excitation and emission wavelengths of 488 nm and 538 nm, respectively. Readings are taken every 2 minutes for 2 hours. Example results of a permeabilization assay are shown in FIG. 1 and Table 2.

A relative permeability index is herein defined wherein the degree of permeabilization of a fungal strain induced by a defined concentration of a defensin is addressed, relative to a value of 1.0 for NaD1 at the same concentration.

FIG. 1 illustrates the relative uptake of SYTOX green into Fov hyphae after treatment with 10 µM NaD1, HXP4, HXL002, HXL007, HXL008 and DmAMP1. See also Table 2. The defensins NaD1, HXP4, HXL002, HXL007 and HXL008 are able to permeabilize Fov hyphae while the defensin DmAMP1 is not. The relative permeability index of each defensin is presented in Table 2. For the purposes of this invention, defensins with a relative permeability index of greater than 0.2 on Fov are considered permeabilizing.

Figure 2:
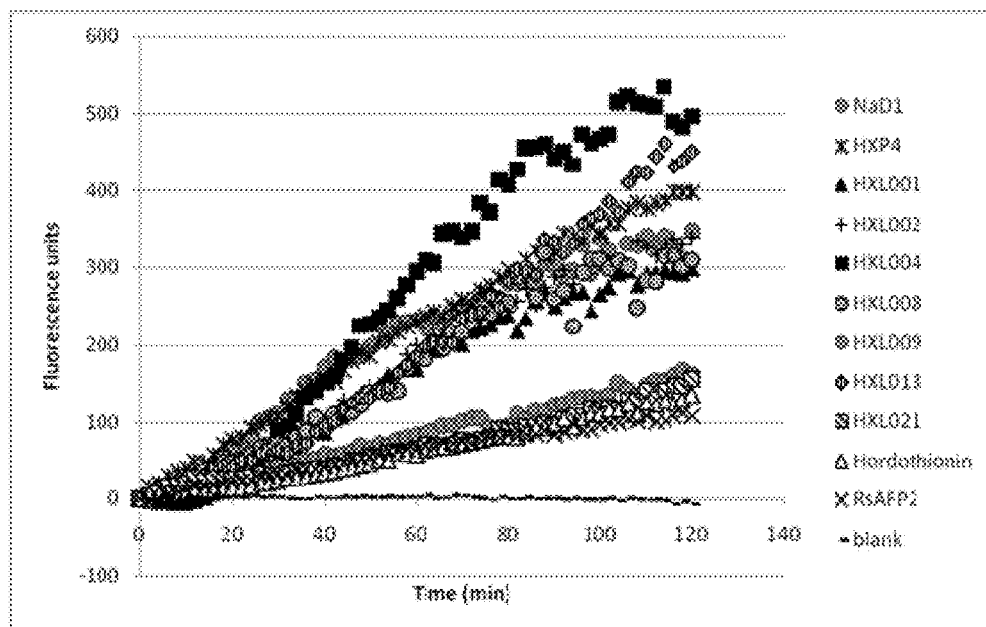
FIG. 2 is a graphical representation of the relative uptake of the green nucleic acid fluorescent dye, SYTOX green [trade mark], into *Fusarium graminearum* (Fgr) treated with NaD1, HXP4, HXL002, HXL007, HXL008, HXL009, HXL013, HXL021, hordothionin and RSAFP2. Reference can also be made to Table 3.

FIG. 2 illustrates the relative uptake of SYTOX green into Fgr hyphae after treatment with 5 µM NaD1, HXP4, HXL001, HXL002, HXL004, HXL008, HXL009, HXL013, HXL021, Hordothionin and RsAFP2. The defensins NaD1, HXP4, HXL002, HXL004 and HXL008 cause significantly more permeabilisation of Fgr hyphae than the defensins HXL009, HXL021, hordothionin and RsAFP2. The relative permeability index of each defensin is presented in Table 3. For the purposes of this invention, defensins with a relative permeability index of greater than 0.5 on Fgr are considered permeabilizing.

Production of Transgenic Plant Cells and/or Tissue

Techniques and agents for introducing and selecting for the presence of heterologous DNA in plant cells and/or tissue are well-known. Genetic markers allowing for the selection of heterologous DNA in plant cells are well-known, e.g. genes carrying resistance to an antibiotic such as kanamycin, hygromycin, gentamicin, or bleomycin. The marker allows for selection of successfully transformed plant cells growing in the medium containing the appropriate antibiotic because they will carry the corresponding resistance gene. In most cases the heterologous DNA which is inserted into plant cells contains a gene which encodes a selectable marker such as an antibiotic resistance marker, but this is not mandatory. An exemplary drug resistance marker is the gene whose expression results in kanamycin resistance, i.e. the chimeric gene containing nopaline synthase promoter n5 neomycin phosphotransferase II and nopaline synthase 3' non-translated region.

Techniques for genetically engineering plant cells and/or tissue with an expression cassette comprising an inducible promoter or chimeric promoter fused to a heterologous coding sequence and a transcription termination sequence are to be introduced into the plant cell or tissue by *Agrobacterium*-mediated transformation, electroporation, microinjection, particle bombardment or other techniques known to the art. The expression cassette advantageously further contains a marker allowing selection of the heterologous DNA in the plant cell, e.g. a gene carrying resistance to an antibiotic such as kanamycin, hygromycin, gentamicin, or bleomycin.

A DNA construct carrying a plant-expressible gene or other DNA of interest can be inserted into the genome of a plant by any suitable method. Such methods may involve, for example, the use of liposomes, electroporation, diffusion, particle bombardment, microinjection, gene gun, chemicals that increase free DNA uptake, e.g. calcium phosphate coprecipitation, viral vectors, and other techniques practiced in the art. Suitable plant transformation vectors include those derived from a Ti plasmid of *Agrobacterium tumefaciens*, such as those disclosed by Herrera-Estrella et al. (1983) *EMBO J* 2:987-995; Bevan et al. (1983) *Nucleic Acids Res* 11(2):369-385; Klee et al. (1985) *Bio/Technology* 3:637-642 and EPO publication 120,516 (Schilperoort et al. European Patent Publication 120, 516). In addition to plant transformation vectors derived from the Ti or root-inducing (Ri) plasmids of *Agrobacterium*, alternative methods can be used to insert the DNA constructs of this invention into plant cells.

The choice of vector in which the DNA of interest is operatively linked depends directly, as is well known in the art, on the functional properties desired, e.g. replication, protein expression, and the host cell to be transformed, these being limitations inherent in the art of constructing recombinant DNA molecules. The vector desirably includes a prokaryotic replicon, i.e. a DNA sequence having the ability to direct autonomous replication and maintenance of the recombinant DNA molecule extra-chromosomally when introduced into a prokaryotic host cell, such as a bacterial host cell. Such replicons are well known in the art. In addition, preferred embodiments that include a prokaryotic replicon also include a gene whose expression confers a selective advantage, such as a drug resistance, to the bacterial host cell when introduced into those transformed cells. Typical bacterial drug resistance genes are those that confer resistance to ampicillin or tetracycline, among other selective agents. The neomycin phosphotransferase gene has the advantage that it is expressed in eukaryotic as well as prokaryotic cells.

Those vectors that include a prokaryotic replicon also typically include convenient restriction sites for insertion of a recombinant DNA molecule of the present invention. Typical of such vector plasmids are pUC8, pUC9, pBR322, and pBR329 available from BioRad Laboratories (Richmond, Calif.) and pPL, pK and K223 available from Pharmacia (Piscataway, N.J.), and pBLUESCRIPT tmand pBS available from Stratagene (La Jolla, Calif.). A vector of the present invention may also be a Lambda phage vector as known in the art or a Lambda ZAP vector (available from Stratagene La Jolla, Calif.). Another vector includes, for example, pCMU (Nilsson et al. (1989) *Cell* 58:707). Other appropriate vectors may also be synthesized, according to known method; for example, vectors pCMU/Kb and pCMUII used in various applications herein are modifications of pCMUIV (Nilsson et al. (1989) supra).

Typical expression vectors capable of expressing a recombinant nucleic acid sequence in plant cells and capable of directing stable integration within the host plant cell include vectors derived from the tumor-inducing (Ti) plasmid of *Agrobacterium tumefaciens*.

A transgenic plant can be produced by any standard means known to the art, including but not limited to *Agrobacterium tumefaciens*-mediated DNA transfer, preferably with a disarmed T-DNA vector, electroporation, direct DNA transfer, and particle bombardment. Techniques are well-known to the art for the introduction of DNA into monocots as well as dicots, as are the techniques for culturing such plant tissues and regenerating those tissues.

Synergy Classification

Synergy is classified as the difference between the observed % fungal growth inhibition caused by the combination of two defensins (Io value) and the expected % fungal growth inhibition of the two defensins based on the sum of the % fungal growth inhibition of each defensin on its own (Ee value calculated according to the Limpel formula used by Richer et al. (1987) supra). The difference, Io-Ee, is the synergy value. A synergy value up to 15 means no significant synergy; 15-30 is a low level of synergy; 30-60 is a medium level of synergy; and >60 is a high level of synergy.

Bioassay Method for In Planta Studies

Preparation of *C. graminicola* Inoculum

*Colletotrichum graminicola* (US isolate Carroll-1A-99) is isolated from *Zea maize* (Pioneer Hi-Bred International, Inc. Johnston, Iowa, USA). Spores are isolated from sporulating cultures grown on V8 agar for approximately 2-3 Weeks. *C. graminicola* spores are collected by scraping the surface of the plates in sterile water and separating spores from hyphal matter by filtration through facial tissue. The concentration of spores in the filtrate is measured using a hemocytometer.

Preparation of *F. graminearum* Inoculum

*Fusarium graminearum* isolate (73B1A) is isolated from *Zea maize* (Pioneer Hi-Bred International, Inc. Johnston, Iowa, USA). Spores are isolated from sporulating cultures grown on SNP agar for approximately 2-3 Weeks. *F. graminearum* spores are collected by scraping the surface of the plates in sterile water. The concentration of spores is measured using a hemocytometer.

Inoculation of Maize Plants

Plants for bioassay are grown in the glasshouse for approximately 6-12 weeks after deflasking.

*C. gramincola* Inoculation

Two wounds, 2.0 mm in length are made on opposing sides of the maize leaf sheath and then overlaid with $1 \times 10^6$ *C. graminicola* spores/mL. Wounds are then sealed with Glad Press'n'Seal for three days. The area of infection is measured by digital photography 10 days post inoculation.

*F. graminearum* Inoculation

Two wounds, 2.0 mm in length are made on opposing sides of the maize leaf sheath. Wounds are overlaid 6 mm diameter paper discs dipped in $1 \times 10^6$ *F. graminearum* spores/mL. Wounds are then sealed with Glad Press'n'Seal for three days. The area of infection is measured by digital photography 10 days post inoculation.

Analysis of Transgene Expression in Corn Plants

ELISA Method

Protein extract: leaf and sheath tissues are excised from plants grown in the glasshouse. The tissue (50 mg) is frozen in liquid nitrogen and ground in a mixer mill (Retsch MM300) for 3×15 seconds at frequency 30 s−1. Protein extracts are made by adding 9 times volume per weight of 2% w/v insoluble PVPP (Polyclar)/PBS/0.05% v/v Tween 20 and vortexing for 20 seconds. The samples are centrifuged for 15 minutes (3,700 rpm) and the supernatant is collected.

ELISA plates (NuncMaxisorp #442404) are incubated with 100 µL/well of primary antibody in PBS (100 ng/well of anti-defensin antibody). Plates are incubated overnight at 4° C. in a humid box. They are then washed for 2 minutes×4 with PBS/0.05% v/v Tween 20. Plates are blocked with 200 µL/well 3% w/v BSA (Sigma A-7030: 98% w/v ELISA grade) in PBS and incubated for 2 hours at 25° C. Plates are then washed for 2 minutes×4 with PBS/0.05% v/v Tween 20.

Corn sheath or leaf protein extracts (100 µL/well diluted in PBS/0.05% v/v Tween 20) are then applied to the plates which are then incubated for 2 hours at 25° C. Plates are then washed for 2 minutes×4 with PBS/0.05% v/v Tween 20 and then 100µL/well of secondary antibody in PBS (e.g. 75 ng/well biotin-labeled defensin antibody) is applied. The biotin labeled antibody is prepared using the EZ-link Sulfo-NHS-LC-biotinylation kit (Pierce); 2 mL of protein A purified antibody and 2 mg of the biotin reagent are used. Plates are incubated for 1 hour at 25° C. and then washed for 2 minutes×4 with PBS/0.05% v/v Tween 20 and 100 µL/well of NeutriAvidin HRP-conjugate (Pierce #31001; 1:1000 dilution; 0.1 µL/well) in PBS is applied. The plates are incubated for 1 hour at 25° C. and then washed for 2 minutes×2 with PBS/0.05% v/v Tween 20, followed by 2 minutes×2 with H2O. Just before use, the substrate is prepared by dissolving 1 ImmunoPure OPD tablet (Pierce #34006) in 9 mL H2O, then adding 1 mL stable peroxide buffer (10×, Pierce #34062). The substrate is applied at 100 µL/well and plates are incubated at 25° C. until color develops (~9 minutes). The reaction is stopped by applying 50 µL 2.5 M sulfuric acid. Absorbance at 490 nm is measured in a plate reader (Molecular Devices).

TABLE 2

| Defensin | Permeability index | |
|---|---|---|
| HXL007 | 1.2 | 350 |
| NaD1 | 1.0 | 300 |
| HXL002 | 0.9 | 260 |
| HXL008 | 0.8 | 225 |
| HXP4 | 0.7 | 220 |
| DmAMP1 | 0.0 | 0 |

TABLE 3

| Defensin | Permeability index | |
|---|---|---|
| HXL004 | 1.6 | 500 |
| HXL013 | 1.4 | 450 |
| HXP4 | 1.3 | 400 |
| NaD1 | 1.0 | 320 |
| HXL002 | 1.0 | 320 |
| HXL001 | 0.9 | 300 |
| HXL008 | 0.9 | 300 |
| HXL021 | 0.5 | 150 |
| HXL009 | 0.4 | 120 |
| Hordothionin | 0.4 | 120 |
| RsAFP2 | 0.3 | 100 |

Example 1

Inhibition of the Growth of Fungal Pathogens in the Presence of a Permeabilizing Defensin and a Non-Defensin Peptide In Vitro Defensins include a Solanaceous Class II defensin (NaD1), an artificial variant (HXP4) and Class I defensins (HXL001, HXL004, HXL008, HXL012, HXL013, HXL015, HXL035) which are permeabilizing defensins. These are partnered with cathelicidins (bactenecin, BMAP28 and LL37), a synthetic variant of bactenecin (Bac2A), a synthetic peptide (CP29), α-hairpinin peptides (Sit_HPN_100A, EcAMP1, Osa_HPN_86B, Sbi_HPN_104C, Sbi_HPN_104I, Cil_HPN_14F), β-hairpin peptides (androctonin and polyphemusin (F12I) and peptides derived from cystatins (SICys9N (67-92), SICys9N (77-110), HvCPI6 (75-99) and CC7 (71-104)).

The inhibitory effects of a permeabilizing defensin in combination with a non-defensin peptide on the growth of *Fusarium graminearum* (*Giberella zea*) (Fgr, Pioneer Hybrid International (PHI) isolate 73B1A), *Fusarium oxysporum* f. sp. *vasinfectum* (Fov, Australian isolate VCG01111 isolated from cotton; from Farming Systems Institute, Department of Agriculture, Fisheries & Forestry, Queensland, Australia), *Colletotrichum graminicola* (Cgr, PHI isolate Carroll-1A-9), *Candida albicans* (isolate DAY185, Department of Biochemistry and Molecular Biology, Monash University, Victoria, Australia), *Cryptococcus gattii* (isolate BAL11), *Trychophyton interdigitale*, *Trichophyton rubrum* and *Microsporum fulvum* (obtained from the National Mycology Reference Centre, South Australia Pathology at the Women's and Children's Hospital, Adelaide, Australia) are measured essentially as described by Broekaert et al. (1990) *FEMS Microbiol Lett* 69:55-59.

Spores are isolated from sporulating fungus spp. growing on synthetic nutrient poor agar (Fgr), V8 agar (Cgr), ½ strength potato dextrose agar (Fov), yeast extract peptone dextrose agar (*Candida albicans, Cryptococcus gattii*) or ½ strength Sabouraud dextrose agar (*Trichophyton interdigitale, Trichophyton rubrum, Microsporum fulvum*). Spores were removed from the plates by the addition of ½ strength potato dextrose broth (PDB). Spore concentrations are measured using a haemocytometer.

Antifungal assays are conducted in 96 well microtitre plates essentially as herein described. Wells are loaded with 10 µL of filter sterilized (0.22 µm syringe filter, Millipore) defensin (10× stock for each final concentration) or water, 10 µL of filter sterilized (0.22 µm syringe filter, Millipore) non-defensin peptide (10× stock for each final concentration) or water and 80 µL of $5 \times 10^4$ spores/mL in ½ strength PDB. The plates are incubated at 25° C. (Fgr, Cgr, Fov) or 30° C. (*C. albicans, C. gattii, T. interdigitale, T. rubrum, M. fulvum*). Fungal growth is assayed by measuring optical density at 595 nm (A595) using a microtitre plate reader (SpectraMax Pro M2; Molecular Devices. Growth is allowed to proceed until the optical density (OD) of the fungus in the absence of any test defensin reached an OD of 0.2. Each test is performed in duplicate.

Synergy is classified as the difference between the observed % fungal growth inhibition caused by the combination of defensin and the non-defensin peptide (Io value) and the expected % fungal growth inhibition of the defensin and the non-defensin peptide based on the sum of the % fungal growth inhibition of each of the defensin and the non-defensin peptide on its own (Ee value calculated according to the Limpel formula used by Richer et al. (1987) supra). The difference, Io-Ee, is the synergy value. A synergy value up to 15 means no significant synergy; 15-30 is a low level of synergy; 30-60 is a medium level of synergy; and >60 is a high level of synergy. Synergy calculations are presented in Tables 4 through 12 wherein, as indicated above, Ee is the expected effect from the additive response according to Limpel's formula expressed as percent inhibition and To is the percent inhibition observed. Synergy occurs when To values are higher than Ee values. The results are shown in Tables 4 through 12.

The results of synergistic inhibition of *Candida albicans* are shown in Table 4.

TABLE 4

*Candida albicans*

| Permeabilizing defensin | AFP | Expected inhibition | Observed inhibition | Synergy |
|---|---|---|---|---|
| NaD1 (2 μM) | CP-29 (2.5 μM) | 14 | 100 | 86 |
| | Bactenecin (2.5 μM) | 31 | 68.3 | 37.3 |
| | Bac2A (2.5 μM) | 7.2 | 46.6 | 39.4 |
| | BMAP28 (2.5 μM) | 10.6 | 65.6 | 55 |
| | LL37 (2.5 μM) | 0.2 | 85.2 | 85 |
| HXP4 (1.25 μM) | EcAMP1 (5 μM) | 19.5 | 100 | 80.5 |
| | Cil_HPN_14F (10 μM) | 13.7 | 61.8 | 48.1 |
| | Osa_HPN_86B (5 μM) | 0 | 98.6 | 98.6 |
| | Sbi_HPN_104I (5 μM) | 0 | 57.4 | 57.4 |
| | Sbi_HPN_104C (5 μM) | 0 | 60.3 | 60.3 |
| | Sit_HPN_100A (5 μM) | 39.3 | 100 | 60.7 |
| | Androctonin (5 μM) | 0 | 96.0 | 96.0 |
| | Polyphemusin (2.5 μM) | 0 | 71.1 | 71.1 |
| HXP4 (2 μM) | CP-29 (2.5 μM) | 26.6 | 100 | 73.4 |
| | Bactenecin (2.5 μM) | 0.0 | 91.1 | 91.1 |
| | Bac2A (2.5 μM) | 59.6 | 86.3 | 26.7 |
| | BMAP28 (2.5 μM) | 41.5 | 95.1 | 53.6 |
| | LL37 (2.5 μM) | 34.1 | 98 | 63.9 |
| HXL001 (4 μM) | CP-29 (2.5 μM) | 25.4 | 98.6 | 73.2 |
| | Bactenecin (2.5 μM) | 37.9 | 74.3 | 36.4 |
| | Bac2A (5 μM) | 43.2 | 98.2 | 55.0 |
| | BMAP28 (5 μM) | 51.6 | 97.1 | 45.5 |
| | LL37 (2.5 μM) | 2.0 | 60.8 | 58.8 |
| HXL004 (2 μM) | CP-29 (2.5 μM) | 36.5 | 99.7 | 63.2 |
| | Bactenecin (2.5 μM) | 24.4 | 71.8 | 47.4 |
| | Bac2A (2.5 μM) | 45.8 | 97.8 | 51.9 |
| | BMAP28 (2.5 μM) | 47.8 | 93.1 | 45.2 |
| | LL37 (2.5 μM) | 48.2 | 93.9 | 45.7 |
| HXL008 (2 μM) | CP-29 (5 μM) | 0.0 | 94.0 | 94.0 |
| | Bac2A (5 μM) | 0.0 | 43.1 | 43.1 |
| | BMAP28 (5 μM) | 3.4 | 69.4 | 66.0 |
| HXL008 (2.5 μM) | EcAMP1 (2.5 μM) | 3 | 82 | 79 |
| | Cil_HPN_14F (5 μM) | 45 | 84 | 39 |
| | Osa_HPN_86B (2.5 μM) | 2 | 97 | 95 |
| | Sbi_HPN_104I (2.5 μM) | 31 | 100 | 69 |
| | Sbi_HPN_104C (5 μM) | 0 | 100 | 100 |
| | Sit_HPN_100A (5 μM) | 33 | 100 | 77 |
| | Androctonin (2.5 μM) | 0 | 100 | 100 |
| | Polyphemusin (2.5 μM) | 0 | 88 | 88 |
| HXL012 (4 μM) | EcAMP1 (5 μM) | 0 | 46.8 | 46.8 |
| | Osa_HPN_86B (2.5 μM) | 0 | 98.2 | 98.2 |
| | Sit_HPN_100A (2.5 μM) | 8.6 | 100.0 | 91.4 |
| | Polyphemusin (0.625 μM) | 0 | 98.5 | 98.5 |
| HXL012 (4 μM) | CP-29 (5 μM) | 0.0 | 100.0 | 100.0 |
| | Bac2A (5 μM) | 31.6 | 75.8 | 44.2 |
| | Bactenecin (5 μM) | 0.0 | 82.0 | 82.0 |
| | BMAP28 (5 μM) | 0.0 | 84.7 | 84.7 |
| HXL013 (1 μM) | CP-29 (5 μM) | 7.6 | 100.0 | 92.4 |
| | Bac2A (2.5 μM) | 13.5 | 93.3 | 79.8 |
| | Bactenecin (2.5 μM) | 29.9 | 82.1 | 52.2 |
| | BMAP28 (2.5 μM) | 38.3 | 99.8 | 61.5 |
| | LL-37 (2.5 μM) | 0.0 | 100.0 | 100.0 |
| HXL015 (1 μM) | CP-29 (0.625 μM) | 0.0 | 59.3 | 59.3 |
| | Bac2A (2.5 μM) | 14.6 | 100.0 | 85.4 |
| | Bactenecin (2.5 μM) | 0.0 | 73.9 | 73.9 |
| | BMAP28 (2.5 μM) | 0.0 | 95.1 | 95.1 |
| | LL-37 (2.5 μM) | 0.0 | 94.4 | 94.4 |
| HXL035 (3 μM) | EcAMP1 (5 μM) | 0.0 | 96.7 | 96.7 |
| | Osa_HPN_86B (2.5 μM) | 35.6 | 94.5 | 58.9 |
| | Sit_HPN_100A (2.5 μM) | 27.0 | 91.1 | 64.1 |

The results of synergistic inhibition of *Cryptococcus gattii* are shown in Table 5.

TABLE 5

| \multicolumn{5}{c}{*Cryptococcus gattii*} |
|---|---|---|---|---|
| Permeabilizing defensin | AFP | Expected inhibition | Observed inhibition | Synergy |
| NaD1 (1 µM) | CP-29 (2.5 µM) | 37.1 | 99.3 | 62.2 |
| | Bactenecin (2.5 µM) | 10.4 | 98.9 | 88.5 |
| | Bac2A (2.5 µM) | 28.6 | 97.6 | 69.0 |
| | BMAP28 (2.5 µM) | 6.3 | 65.7 | 59.3 |
| | LL37 (2.5 µM) | 0.0 | 92.9 | 92.9 |
| HXP4 (0.5 µM) | CP-29 (2.5 µM) | 6.9 | 93.0 | 86.1 |
| | Bactenecin (2.5 µM) | 0.2 | 97.9 | 97.7 |
| | LL37 (2.5 µM) | 35.9 | 100.0 | 64.1 |
| HXP4 (1 µM) | Bac2A (2.5 µM) | 76.3 | 99.0 | 22.7 |
| | BMAP28 (2.5 µM) | 23.3 | 95.3 | 72.1 |

The results of synergistic inhibition of *Fusarium graminearum* are shown in Table 6.

TABLE 6

| \multicolumn{5}{c}{*Fusarium graminearum*} |
|---|---|---|---|---|
| Permeabilizing defensin | AFP | Expected inhibition | Observed inhibition | Synergy |
| HXP4 (0.15 µM) | EcAMP1 (0.625 µM) | 20.1 | 95.5 | 75.5 |
| | Cil_HPN_14F (2.5 µM) | 34.5 | 94.6 | 60.1 |
| | Osa_HPN_86B (1.25 µM) | 29.4 | 98.8 | 69.5 |
| | Sbi_HPN_104I (5 µM) | 43.1 | 96.8 | 53.7 |
| | Sbi_HPN_104C (2.5 µM) | 22.5 | 97.9 | 75.4 |
| | Sit_HPN_100A (0.625 µM) | 39.1 | 98.9 | 59.8 |
| | Androctonin (5 µM) | 28.6 | 94.2 | 65.7 |
| | Polyphemusin (0.625 µM) | 55.8 | 98.6 | 42.8 |
| HXP4 (0.25 µM) | CP-29 (0.5 µM) | 75.3 | 108.4 | 33.2 |
| | Bactenecin (0.5 µM) | 61.6 | 98.0 | 36.4 |
| | Bac2A (2.5 µM) | 58.4 | 100.0 | 41.6 |
| | BMAP28 (2.5 µM) | 50.9 | 100.0 | 49.1 |
| | EcAMP1 (4 µM) | 5.7 | 94.6 | 88.9 |
| NaD1 (1 µM) | EcAMP1 (4 µM) | 21.5 | 95.1 | 73.6 |
| HXL001 (4 µM) | EcAMP1 (4 µM) | 0.0 | 77.2 | 77.2 |
| HXL004 (0.5 µM) | Bactenecin (1.25 µM) | 4.1 | 70.9 | 66.8 |
| | BMAP28(5 µM) | 3.0 | 89.1 | 86.1 |
| | LL-37(2.5 µM) | 4.9 | 77.2 | 72.3 |
| HXL004 (1 µM) | EcAMP1 (4 µM) | 5.3 | 83.5 | 78.2 |
| HXL008 (0.5 µM) | EcAMP1 (5 µM) | 20.0 | 60.7 | 40.6 |
| | Cil_HPN_14F (5 µM) | 32.7 | 53.6 | 20.9 |
| | Osa_HPN_86B (5 µM) | 12.3 | 89.7 | 77.4 |
| | Sbi_HPN_104I (10 µM) | 34.3 | 97.9 | 63.6 |
| | Sbi_HPN_104C (5 µM) | 28.2 | 81.0 | 52.8 |
| | Sit_HPN_100A (5 µM) | 43.9 | 98.4 | 54.5 |
| | Androctonin (2.5 µM) | 40.9 | 89.0 | 48.1 |
| | Polyphemusin (0.625 µM) | 56.9 | 99.0 | 42.2 |
| HXL008 (1 µM) | CP-29 (0.625 µM) | 11.3 | 49.9 | 38.6 |
| | Bactenecin (0.625 µM) | 13.6 | 42.3 | 28.7 |
| | BMAP28(5 µM) | 22.9 | 41.2 | 18.3 |
| | LL-37(5 µM) | 7.1 | 62.3 | 55.2 |
| HXL015 (0.5 µM) | LL-37 (2.5 µM) | 0.0 | 95.4 | 95.4 |
| HXL015 (1 µM) | CP-29 (0.625 µM) | 69.0 | 93.6 | 24.6 |
| | Bactenecin (1.25 µM) | 53.1 | 93.7 | 40.6 |
| | BMAP28 (2.5 µM) | 49.0 | 98.4 | 49.4 |

The results of synergistic inhibition of *Trichophyton interdigitale* are shown in Table 7.

TABLE 7

| \multicolumn{5}{c}{*Trichophyton interdigitale*} |
|---|---|---|---|---|
| Permeabilizing defensin | AFP | Expected inhibition | Observed inhibition | Synergy |
| NaD1 (1 µM) | CP-29 (2.5 µM) | 46.5 | 85.2 | 38.7 |
| | BMAP28 (4 µM) | 36.0 | 83.1 | 47.1 |
| | LL37 (2.5 µM) | 25.2 | 75.8 | 50.6 |
| HXP4 (1 µM) | CP-29 (2.5 µM) | 53.0 | 88.2 | 35.3 |
| HXL001 (2 µM) | CP-29 (5 µM) | 24.2 | 66.1 | 41.9 |
| | Bactenecin(2.5 µM) | 32.7 | 62.0 | 29.3 |
| | LL37 (5 µM) | 20.4 | 64.3 | 43.9 |
| HXL004 (2 µM) | Bactenecin (0.625 µM) | 24.4 | 86.0 | 61.6 |
| | BMAP28 (2.5 µM) | 38.9 | 80.0 | 41.1 |
| HXL004 (1 µM) | LL37 (5 µM) | 32.9 | 59.0 | 26.1 |
| HXL008 (0.5 µM) | CP-29 (2.5 µM) | 39.9 | 74.2 | 34.3 |
| | Bactenecin(2.5 µM) | 56.3 | 86.7 | 30.4 |
| | BMAP28 (2.5 µM) | 45.7 | 63.9 | 18.2 |
| | LL37 (2.5 µM) | 30.4 | 73.2 | 42.8 |
| HXL012 (2 µM) | CP-29 (5 µM) | 17.8 | 71.7 | 53.9 |

The results of synergistic inhibition of *Microsporum fulvum* are shown in Table 8.

TABLE 8

Microsporum fulvum

| Permeabilizing defensin | AFP | Expected inhibition | Observed inhibition | Synergy |
|---|---|---|---|---|
| NaD1 (0.5 μM) | CP-29 (1.25 μM) | 47.8 | 66.7 | 18.9 |
| | Bactenecin (2.5 μM) | 1.6 | 43.6 | 42 |
| | BMAP28 (2.5 μM) | 0.0 | 36.5 | 36.5 |

The results of synergistic inhibition of *Fusarium oxysporum* f sp. *Vasinfectum* are shown in Table 9.

TABLE 9

Fusarium oxysporum f. sp. vasinfectum

| Permeabilizing defensin | AFP | Expected inhibition | Observed inhibition | Synergy |
|---|---|---|---|---|
| NaD1 (1 μM) | Bactenecin (2.5 μM) | 33.9 | 66 | 32.1 |
| | BMAP28 (5 μM) | 24.2 | 47.8 | 23.6 |
| | LL-37 (5 μM) | 20.3 | 62.8 | 42.5 |
| HXP4 (0.25 μM) | CP-29 (2.5 μM) | 19.2 | 56 | 36.8 |
| | Bactenecin (5 μM) | 14.3 | 64.8 | 50.5 |
| | BMAP28 (5 μM) | 15.6 | 54.3 | 38.7 |
| | LL-37 (2.5 μM) | 21.3 | 91.9 | 70.6 |
| HXL001 (4 μM) | CP-29 (5 μM) | 62.2 | 90.4 | 28.2 |
| | Bactenecin (5 μM) | 44.1 | 88.9 | 44.8 |
| | BMAP28 (5 μM) | 22.4 | 82.5 | 60.1 |
| | LL-37 (5 μM) | 15 | 59.9 | 44.9 |
| HXL004 (1 μM) | CP-29 (5 μM) | 28.5 | 68.6 | 40.1 |
| | Bactenecin (5 μM) | 24.8 | 76.4 | 51.6 |
| | BMAP28 (5 μM) | 13.5 | 46.5 | 33 |
| | LL-37 (5 μM) | 12.3 | 69.8 | 57.5 |
| HXL008 (2 μM) | Bactenecin (5 μM) | 24.1 | 76.4 | 52.3 |
| | LL-37 (5 μM) | 21.4 | 72.8 | 51.4 |
| HXL013 (4 μM) | CP-29 (5 μM) | 34.2 | 100 | 65.8 |
| | BMAP28 (5 μM) | 21.4 | 62.5 | 41.1 |

The results of synergistic inhibition of *Colletotrichum graminicola* are shown in Table 10.

TABLE 10

Colletotrichum graminicola

| Permeabilizing defensin | AFP | Expected inhibition | Observed inhibition | Synergy |
|---|---|---|---|---|
| NaD1 (2.5 μM) | CP-29 (5 μM) | 32 | 87.4 | 55.4 |
| | Bactenecin (2.5 μM) | 19.7 | 58.5 | 38.8 |
| | BMAP28 (5 μM) | 57.1 | 83.3 | 26.2 |
| | LL-37 (2.5 μM) | 4.4 | 77.3 | 72.9 |
| HXL001 (2.5 μM) | CP-29 (5 μM) | 20.8 | 61.1 | 40.3 |
| | Bactenecin (5 μM) | 22.1 | 69.7 | 47.6 |
| | BMAP28 (5 μM) | 26.9 | 54 | 27.1 |
| | LL-37 (5 μM) | 30.8 | 86.8 | 56 |
| HXL004 (1.25 μM) | CP-29 (5 μM) | 30.5 | 99.3 | 68.8 |
| | Bactenecin (5 μM) | 50.8 | 78.3 | 27.5 |
| | BMAP28 (5 μM) | 34.7 | 85.4 | 50.7 |
| | LL-37 (5 μM) | 34.6 | 71.1 | 36.5 |
| HXL008 (2.5 μM) | CP-29 (5 μM) | 55.2 | 92.9 | 37.7 |
| | Bactenecin (5 μM) | 56.6 | 93.2 | 36.6 |
| | BMAP28 (5 μM) | 48.9 | 98.9 | 50 |
| | LL-37 (2.5 μM) | 61.4 | 90.7 | 29.3 |

The results of synergistic inhibition of *Fusarium graminearum* are shown in Table 12.

TABLE 11

Fusarium graminearum

| Permeabilizing defensin | AFP | Expected inhibition | Observed inhibition | Synergy |
|---|---|---|---|---|
| NaD1 (0.125 μM) | SlCys9N$_{67-92}$ (0.5 μM) | 28 | 83 | 55 |
| | SlCys9N$_{77-110}$ (0.5 μM) | 30 | 76 | 46 |
| | HvCPI6$_{75-99}$ (1.0 μM) | 13 | 94 | 81 |
| | CC7$_{77-104}$ (0.5 μM) | 27 | 97 | 70 |

The results of synergistic inhibition of *Candida albicans* are shown in Table 12.

TABLE 12

Candida albicans

| Permeabilizing defensin | AFP | Expected inhibition | Observed inhibition | Synergy |
|---|---|---|---|---|
| HXP4 (2 μM) | SlCys9N$_{67-92}$ (2.5 μM) | 11.3 | 92.7 | 81.4 |
| | HvCPI6$_{75-99}$ (2.5 μM) | 0 | 65.6 | 65.6 |
| | CC7$_{77-104}$ (10 μM) | 9.6 | 71.7 | 62.1 |
| HXL008 (2 μM) | SlCys9N$_{67-92}$ (5 μM) | 5.3 | 96.8 | 91.5 |
| | HvCPI6$_{75-99}$ (5 μM) | 0 | 83.4 | 96.4 |

Example 2

Inhibition of Growth of Fungal Pathogens in the Presence of an α-Hapirpinin or β-Hairpin Some α-hairpinin and β-hairpin peptides show efficacy on their own against pathogens at a concentration higher than the concentration used in a combination with a plant defensin. At the concentration used in the combination the α-hairpinin or β-hairpin peptide exhibits no or minimal anti-pathogen activity. The results are shown in Table 13.

TABLE 13

IC$_{50}$ Values

| | IC50 | | | | |
|---|---|---|---|---|---|
| Hairpinin | *Cgr* | *Fgr* | *S. cer* | *C. alb* | *T. rub* |
| CilHPN_14F | | | 12 μM | | |
| OsaHPN_86B | 13 μM | 18 μM | 8 μM | 9 μM | |
| SitHPN_100A | 14 μM | 8 μM | 8 μM | 8 μM | 20 μM |
| SbiHPN_104C | 16 μM | 7 μM | >20 μM | 7 μM | |
| SbiHPN_104I | | | >20 μM | | |
| EcAMP1 | 20 uM | 7 μM | 8 μM | 8 μM | |
| Androctonin | 13 μM | 7 μM | | 7 μM | 1 μM |
| Polyphemusin I | 6 μM | 3 μM | | 4 μM | 1 μM |

*Cgr*—Colletotrichum graminicola
*Fgr*—Fusarium greaminearum
*S. cer*—Saccharomyces cerevisiae
*C. alb*—Candida albicans
*T. rub*—Trichophyton rubrum Those skilled in the art will appreciate that the disclosure described herein is susceptible to variations and modifications other than those specifically described. It is to be understood that the disclosure contemplates all such variations and modifications. The disclosure also enables all of the steps, features, compositions and compounds referred to or indicated in this specification, individually or collectively, and any and all combinations of any two or more of the steps or features or compositions or compounds.

BIBLIOGRAPHY

Alexander et al. (1993) *Proc Natl Acad Sci USA* 90:7327-7371
Bevan et al. (1983) *Nucleic Acids Res* 11(2):369-385
Bloch and Richardson (1991) *FEBS Lett* 279(1):101-104
Broekaert et al. (1990) *FEMS Microbiol Lett* 69:55-59
Colilla et al. (1990) *FEBS Lett* 270(1-2):191-194
Gao et al. (2000) *Nat Biotechnol* 18(12):1307-1310
Gaspar et al. (2014) *J Exp Bot* February 6 epub
Gorlach et al. (1996) *Plant Cell* 8:629-643
Greco et al. (1995) *Pharmacol Rev.* 47:331-385
Hayes et al. (2014) *Cell Molecule Life Sci* February 2014, Online issue 1420-682X
Herrera-Estrella et al. (1983) *EMBO J* 2:987-995
Janssen et al. (2003) *Biochemistry* 42(27):8214-8222
Jha et al. (2009) *Transgenic Res* 18(0:59-69
Klee et al. (1985) *Bio/Technology* 3:637-642
Lay et al. (2003) *Plant Physiol* 131(3):1283-1293
Nilsson et al. (1989) *Cell* 58:707
Oerke and Dehne (2004) *Crop Protection* 23:275-285
Richer (1987) *Pestic Sci* 19:309-315
Spelbrink et al. (2004) *Plant Physiol* 135(4):2055-2067
Uknes et al. (1993) *Molecular Plant Microbe Interaction* 6:680-685
van der Weerden et al. (2008) *J Biol Chem* 283(21):14445-14452
van der Weerden et al. (2010) *J Biol Chem* 285(48): 37513-37520
van der Weerden et al. (2013) *Cell Molecule Life Sci* 70(19) 3545-3570
Yount and Yeaman (2005) *Protein Pept Lett* 12(1):49-67

What is claimed is:

1. A method for inhibiting growth or infection or infestation of a fungal pathogen on or in a subject, said method comprising contacting the pathogen with an effective amount of a combination of a plant permeabilizing defensin selected from the group consisting of NaD1(*Nicotiana alata* defensin),TPP3(tomato defensin), PhD1(*Petunia hybria* defesin 1), PhD1A(SEQ ID NO:47), PhD2(*Petunia hybria* defesin 2), FST(flower-specific defensin), NoD173(SEQ ID NO:48), HXL001(SEQ ID NO:25), HXL002(SEQ ID NO:26), HXL004(SEQ ID NO:27), HXL007(SEQ ID NO:28), HXL008(SEQ ID NO:29), HXL012(SEQ ID NO:32), HXL013(SEQ ID NO:30), HXL015(SEQ ID NO:31), HXL035(SEQ ID NO:33), HXL036(SEQ ID NO:34) and a defensin variant comprising a Loop1B from a Class I defensin replacing the corresponding Loop 1B from a Solanaceous Class II defensin and a non-defensin peptide selected from the group consisting of a cathelicidin peptide, a hairpin peptide, a hairpin peptide from which disulfide bridges have been removed, synthetic peptide CP-29, and a peptide derived from a cystatin, the combination of the defensin and peptide being synergistic compared to the use of each alone at the same individual dose as used in the combination.

2. The method of claim 1 wherein the defensin variant is selected from the group consisting of HXP4 (SEQ ID NO:8), HXP34 (SEQ ID NO:15), HXP35 (SEQ ID NO:16), HXP37 (SEQ ID NO:17), HXP58 (HQ ID NO:18), HXP72 (SEQ ID NO:19), HXP91 (SEQ NO:20), HXP92 (SEQ ID NO:21), HXP95 (SEQ ID NO:22) and HXP107 (SEQ ID NO:23).

3. The method of claim 1 wherein the cathelicidin peptide is selected from the group consisting of bactenecin, LL-37, BMAP28, SMAP29, PMAP23, mCRAMP, RK-31 and KS-30.

4. The method of claim 1, wherein the hairpin peptide is an α-hairpinin selected from the group consisting of Sit_HPN_100A(SEQ ID NO:35), EcAMP1(SEQ ID NO:36), Osa_HPN_86B(SEQ ID NO:37), Sbi_HPN_104C (SEQ ID NO:38), Sbi_HPN_104I(SEQ ID NO:39), Cil_HPN_14F(SEQ ID NO:40), BWI-2c(Buckwheat trypsin inhibitor-2c), BWI-2b(Buckwheat trypsin inhibitor-2b), luffin P1 from *Luffa aegytiaca*, MBP1(maize basic peptide 1), MiAMP2d(*Macadamia integrifolia* antimicrobial peptide 2d), C2(Cys-rich domin peptide 2 from Cucurbita maxima and VhTI(*Veronica hederifolia*trypsin inhibitor).

5. The method of claim 1 wherein the hairpin peptide is a β-hairpin selected from the group consisting of androctonin, bactenecin, polyphemusin (F12I), polyphemusin I, polyphemusin II, tachyplesin II, gomesin, thanatin and protegrin.

6. The method of claim 1 wherein the peptide with disulfide bridges removed is Bac2A or EcAMP4A.

7. The method of claim 1 wherein the peptide derived from a cystatin is selected from the group consisting of SlCys9N (67-92), SlCys9N(77-110), HvCPI6(75-99) and CC7(71-104).

8. The method of Claim 1, wherein the fungal organism is selected from the group consisting of a species of *Absidia* spp, *Acremonium* spp, *Alternaria* spp, *Apophysomyces* spp, *Aspergillus* spp, *Basidiobolus* spp, *Bipolaris* spp, *Blastomyces* spp, *Botrytis* spp, *Candida* spp, *Cercospora* spp, *Chaetomium* spp, *Cladophialophora* spp, *Cochliobolus* spp, *Coccidioides* spp, *Colletotrichum* spp, *Conidiobolus* spp, *Cryptococcus* spp, *Cunninghamella* spp, *Dacrlaria* spp, Dematiaceous molds, *Diaporthe* spp, *Epidermophyton* spp, *Erysiphe* spp, *Exserohilium* spp, *Fusarium* spp, *Gaeumannomyces* spp, *Histoplasma* spp, *Leptosphaeria* spp, *Macrophomina* spp, *Microsporum* spp, *Mucor* spp, *Mycosphaerella* spp, *Paeciliomyces* spp, *Paracoccidioides* spp, *Penicillium* spp, *Phakopsora* spp, *Phialophora* spp, *Phoma* spp, *Phytophthora* spp, *Pneumocystis* spp, *Pseudallescheria* spp, *Puccinia* spp, *Phymatotrichopsis* spp, *Plasmodiophora* spp, Puccinia spp, *Pythium* spp, *Ramichloridium* spp, *Rhizoctonia* spp, *Rhizopus* spp, *Rhizomucor* spp, *Saksenaea* spp, *Scedosporium* spp, *Sclerotinia* spp, *Septoria* spp, *Sporothrix* spp, *Stachybotrys* spp, *Stenocarpella* spp, *Syncephalastrum* spp, *Thielaviopsis* spp, *Tilletia* spp, *Trichophyton* spp, *Trichosporon* spp, *Ustilago* spp, *Verticillium* spp, and rust fungi.

9. The method of claim 8 wherein the fungal organism is selected from the group consisting of *Absidia corymbifera, Apophysomyces elegans, Acremonium strictum, Alternaria alternata, Alternaria brassicicola, Alternaria macrospora, Alternaria raphani, Aspergillus fumigatus, Aspergillus niger, Aspergillus flavus, Aspergillus nidulans, Aspergillus paraciticus, Basidiobolus ranarum, Bipolaris spp, Blastomyces dermatitidis, Botrytis cinerea, Candida albicans, Candida dubliniensis, Candida famata, Candida glabrata, Candida guilliermondii, Candida haemulonii, Candida kefyr, Candida krusei, Candida lusitaniae, Candida norvegensis, Candida parapsilosis, Candida tropicalis, Candida viswanathii, Cercospora beticola, Cercospora gossypina, Cercospora sojina, Cercospora zeae maydis, Chaetomium atrobrunneum, Cladophialophora bantiana, Cochliobolus heterostrophus, Coccidioides immitis, Coccidioides posadasii, Colletotrichum graminicola, Cokeromyces recurvatus, Conidiobolus coronatus, Conidiobolus incongruus, Cryptococcus neoformans, Cryptococcus gattii, Cryptococcus grubii, Cunninghamella bertholletiae, Dactlaria gallopavum, Diaporthe phaseolorum, Epidermophyton floccosum, Erysiphe graminis (Blumeria graminis), Exserohilum rostratum Exserohilum turcicum, Fusarium avenaceum, Fusarium oxysporum, Fusarium oxysporum f. sp. vasinfectum (Fov), Fusarium graminearum, Fusarium culmorum, Fusarium oxysporum f. sp. dianthi, Fusarium oxysporum f. sp. lycopersici, Fusarium pseudograminearum, Fusarium verticilloides, Fusarium solani, Fusarium monoliforme, Gaeumannomyces graminis var. tritici, Histoplasma capsulatum, Leptosphaeria maculans, Macrophomina phaseolina, Microsporum canis, Microsporum gypseum, Mucor indicus, Mycosphaerella zeae, Paecilomyces variotii, Paecilomyces lilacinus, Paracoccidioides brasiliensis, Pseudallescheria boydii, Penicillium marneffei, Phialophora gregata, Phakopsora pachyrhizi, Phytophthora sojae, Phoma exigua, Puccinia schedonnardii, Puccinia cacabata, Phymatotrichopsis omnivora, Plasmodiophora brassicae, Puccinia graminis, Puccinia triticina, Puccinia sorghi, Ramichloridium obovoideum, Rhizoctonia cerealis, Rhizopus oryzae, Rhizomucor pusillus, Rhizoctonia solani, Saksenaea vasiformis, Sclerotinia sclerotiorum, Septoria tritici, Septoria nodorum, Scedosporium apiospermum, Scedosporium prolificans, Sporothrix schenckii, Stenocarpella (Diplodia) maydis, Syncephalastrum racemosum, Thielaviopsis basicola, Tilletia controversa, Tilletia indica, Tilletia caries Trychophyton rubrum, Trychophyton mentagrophytes, Trychophyton interdigitales, Trychophyton tonsurans, Tricosporon beigelii, Trichosporon asahii, Trichosporon inkin, Trichosporon asteroides, Trichosporon cutaneum, Trichosporon domesticum, Trichosporon mucoides, Trichosporon ovoides, Trichosporon pullulans, Trichosporon loubieri, Trichosporon japonicum, Ustilago tritici, Ustilago zeae, Verticillium dahliae* and *Wangiella dermatitidis*.

10. The method of claim 1, wherein the defensin and peptide are topically applied to a human, animal or plant, or in an environmental locale.

11. The method of claim 1, wherein the subject is a human.

12. A method for treatment or prophylaxis of a fungal pathogen of a human or animal subject, comprising inhibiting growth or infection or infestation of the pathogen on or in the subject according to the method of claim 1.

13. A method for inhibiting growth or infection or infestation of a fungal pathogen, said method comprising contacting the pathogen with an effective amount of a combination of a plant permeabilizing defensin selected from the group consisting of NaD1(*Nicotiana alata* defensin), TPP3 (tomato defensin), PhD1(*Petunia hybrida* defensin1), PhD1A(SEQ ID NO:47), PhD2(*Petunia hybrida* defensin 2),FST(flower-specific defensin), NoD173(SEQ ID NO:48), HXL001(SEQ ID NO:25), HXL002(SEQ ID NO:26), HXL004(SEQ ID NO:27), HXL007(SEQ ID NO:28), HXL008(SEQ ID NO:29), HXL0012(SEQ ID NO:32), HXL013(SEQ ID NO:30), HXL015(SEQ ID NO:31), HXL035(SEQ ID NO:33), HXL036(SEQ ID NO:34) and a variant or derivative of a defensin selected from the group consisting of HXP4(SEQ ID NO:8), HXP34(SEQ ID NO:15), HXP35(SEQ ID NO:16), HXP37(SEQ ID NO:17), HXP58(SEQ ID NO:18), HXP72(SEQ ID NO:19),HXP91 (SEQ ID NO:20), HXP92(SEQ ID NO:21), HXP95(SEQ ID NO:22), and HXP107(SEQ ID NO:23), and a non-defensin peptide selected from the group consisting of a cathelicidin peptide, a hairpin peptide, a hairpin peptide from which disulfide bridges have been removed, synthetic peptide CP-29 and a peptide derived from cystatin, the combination of the defensin and the peptide being synergistic compared to the use of each alone at the same individual dose as used in the combination.

* * * * *